US010934524B2

(12) United States Patent
Adam et al.

(10) Patent No.: US 10,934,524 B2
(45) Date of Patent: Mar. 2, 2021

(54) HIGH THROUGHPUT MONOCLONAL ANTIBODY GENERATION BY B CELL PANNING AND PROLIFERATION

(71) Applicant: EPITOMICS, INC., Burlingame, CA (US)

(72) Inventors: Luc Adam, Hayward, CA (US); Karin Vroom, South San Francisco, CA (US); Liang Xiang, Burlingame, CA (US); Li Wei, Hangzhou (CN); Weimin Zhu, San Francisco, CA (US)

(73) Assignee: EPITOMICS, INC., Burlingame, CA (US)

( * ) Notice: Subject to any disclaimer, the term of this patent is extended or adjusted under 35 U.S.C. 154(b) by 77 days.

(21) Appl. No.: 15/554,699

(22) PCT Filed: Mar. 11, 2016

(86) PCT No.: PCT/US2016/022181
§ 371 (c)(1),
(2) Date: Aug. 30, 2017

(87) PCT Pub. No.: WO2016/149137
PCT Pub. Date: Sep. 22, 2016

(65) Prior Publication Data
US 2018/0201900 A1 Jul. 19, 2018

Related U.S. Application Data

(60) Provisional application No. 62/135,084, filed on Mar. 18, 2015.

(51) Int. Cl.
*C12N 5/0781* (2010.01)
*C07K 16/00* (2006.01)

(52) U.S. Cl.
CPC ............ *C12N 5/0635* (2013.01); *C07K 16/00* (2013.01); *C07K 2317/14* (2013.01)

(58) Field of Classification Search
CPC ... C12N 5/0635; C07K 16/00; C07K 2317/14
See application file for complete search history.

(56) References Cited

U.S. PATENT DOCUMENTS

| 7,790,414 B2 | 9/2010 | Lawson et al. |
| 2011/0312505 A1 | 12/2011 | Reddy et al. |
| 2012/0214192 A1 | 8/2012 | Kitamura et al. |
| 2013/0316353 A1 | 11/2013 | Carvalho-Jensen et al. |
| 2014/0287952 A1 | 9/2014 | Allison et al. |

FOREIGN PATENT DOCUMENTS

| CN | 102839152 A | 12/2012 |
| EP | 2703485 A1 | 3/2014 |
| WO | WO 2008/045140 A1 | 4/2008 |
| WO | WO 2012/178150 A2 | 12/2012 |

OTHER PUBLICATIONS

Cocco et al., "In Vitro Generation of Long-lived Human Plasma Cells", The Journal of Immunology, 2012, 189(12):5773-5785.
Georgiou et al., "The promise and challenge of high-throughput sequencing of the antibody repertoire", Nature Biotechnology, 2014, 32(2):158-168.
Kodituwakku et al., "Isolation of antigen-specific B cells", Immunology and Cell Biology, 2003, 81:163-170.
Kondo et al., "CD40-activated B cells can be generated in high number and purity in cancer patients: analysis of immunogenicity and homing potential", Clinical & Experimental Immunology, The Journal of Translational Immunology, 2008, 155: 249-256.
Kooten et al., "CD40-CD40 ligand", Journal of Leukocyte Biology, 2000, 67:2-17.
Liebig et al., "Murine Model of CD40-activation of B cells", Journal of Visualized Experiments, 2010, 37, http://www.iove.com/details.php?id=1734, doi: 10.3791/1734.
Lightwood et al., "Antibody generation through B cell panning on antigen followed by in situ culture and direct RT-PCR on cells harvested en masse from antigen-positive wells", Journal of Immunological Medthods, 2006, 316:133-143.
Miltenyi Biotec, "Anti-Biotin MicroBeads", MACS Miltenyi Biotech, 2014, retrieved from https://web.archive.org/web/20141024130646/ttp://www.miltenyibiotec.com/en/products-and-services/macs-cell-separation/cell-separation-reagents/any-cell-type/anti-biotin microbeads.aspx.
Reddy et al., "Monoclonal antibodies isolated without screening by analyzing the variable-gene repertoire of plasma cells", Nature Biotechnology, 2010, 28(9):965-969.
Seeber et al., "A Robust High Throughput Platform to Generate Functional Recombinant Monoclonal Antibodies Using Rabbit B Cells from Peripheral Blood", Plos One, 2014, 9(2):e86184.
Wykes, "Why do B cells produce CD40 ligand?" Immunology and Cell Biology, 2003, 81:328-331.
Scornavacca et al., "Tanglegrams for rooted phylogenetic trees and networks", Bioinformatics, 2011, 27(13): i248-i256.
Smith et al., "Detection and Enrichment of Rare Antigen-specific B Cells for Analysis of Phenotype and Function", Journal of Visualized Experiments, Author manuscript, 2017, No. 120, p. e55382.

(Continued)

*Primary Examiner* — Sharon X Wen
(74) *Attorney, Agent, or Firm* — James S. Keddie; Bozicevic, Field & Francis LLP

(57) ABSTRACT

Provided herein, inter alia, is a method for producing an enriched population of antigen-specific plasma cells. In some embodiments, the method may comprise: (a) obtaining a sample of cells from an animal that has been immunized by an antigen, wherein the sample comprises B cells; (b) enriching for a population of antigen-specific B cells that comprise cell surface antibodies that are specific for the antigen by: i. contacting at least 105 of the cells in said sample, en masse, with the antigen or a portion thereof; and ii. isolating cells that bind to the antigen or portion thereof; and (c) activating the enriched B cells, en masse, in the presence of the antigen or portion thereof, to produce the enriched population of antigen-specific plasma cells.

15 Claims, 12 Drawing Sheets

Specification includes a Sequence Listing.

(56) References Cited

OTHER PUBLICATIONS

Liang et al., "Establishment of a method for expanding and differentiating the peripheral blood B lymphocytes into plasma cells via in vitro induction and Evaluation of the same", Int J Immunol, 2013, 36(2): 149-162.
Lv et al., Research progress on memory B cell immune response mechanism, 2015, 31(2): 267-273, doi: 10. 3969/j.issn. 1000-484X. Feb. 28, 2005.

tanglegram unordered (A)

Proliferated cells culture captured by panning

Flow-through Cell culture

Forward/side scatter plot    Intracellular IgG-Fc (B)

Intracellular IgG interacting with KLH-antigen

HIGH THROUGHPUT MONOCLONAL ANTIBODY GENERATION BY B CELL PANNING AND PROLIFERATION

CROSS-REFERENCING

This application is a § 371 national phase of International Application No. PCT/US2016/022181, filed on Mar. 11, 2016, which claims the benefit of U.S. provisional application Ser. No. 62/135,084, filed on Mar. 18, 2015, which applications are incorporated by reference herein.

BACKGROUND

The ability of mammals to generate a very diverse repertoire of antibodies in response to immunization by antigen has been exploited in a wide range of fields, including diagnostics and therapy. Hybridoma technology was developed by Kohler and Milstein several decades ago and today several low-throughput methods for generating monoclonal antibodies have been developed. Such methods include B-cell immortalization, cloning of antibody-encoding genes and cDNAs by single-cell PCR and in vitro "combinatorial" methods that require the production huge recombinant antibody libraries.

High throughput antibody-discovery methods have been slow to develop because, based on sequence information alone, it is impossible to determine the antigen to which an antibody binds and which heavy and light chains should be paired together.

Lightwood (J. Immun. Methods 2006 316: 13-143) describes a method for generating high-affinity monoclonal antibodies. In Lightwood's method, a relatively small number of B cells from an immunized rabbit are placed into each well of a multi-well ELISA plate that contains a coating of solid phase antigen. After extensive washing to remove non-bound cells as well as B cells that bound with low affinity, the retained B cells were cultured for 7 days to induce proliferation and secretion of immunoglobulin. Supernatants were screened to identify which wells of the plate contain antigen-specific antibodies. Single heavy- and light chain variable region genes were recovered from individual wells by RT-PCR, and sequenced. The Lightwood method, because it requires depositing a relatively small, titrated, amount of B cells into the wells of a 96-well plate, screening supernatants, and performing PCR on cells harvested from individual wells, is inherently low throughput. Moreover, Lightwood's method requires a single activated B cell or a relatively small number of activated B cells per well, because the heavy and light chain pairing would otherwise be unknown. Further, the number of activated B cells produced using the Lightwood method is insufficient for the production of hybridomas on a commercial scale.

Reddy (Nat. Biotechnol. 2010 28:965-9) describes a bioinformatics-based method to mine antibody variable region-gene repertoires from bone marrow plasma cells (BMPCs) of immunized mice. Reddy discovered that the antibody repertoire of bone marrow plasma cells becomes highly polarized after immunization, with the most abundant sequences represented at frequencies between about 1% to over 10% of the total repertoire. Reddy paired the most abundant variable heavy (VH) and variable light (VL) genes based on their relative frequencies, reconstructed them using automated gene synthesis, and expressed recombinant antibodies in bacteria or mammalian cells. Antibodies generated in this manner from six mice, each immunized with one of three antigens, were mostly antigen specific (21/27 or 78%). Bone marrow plasma cells are not readily accessible, since their isolation requires animal euthanization and selection of $CD138^+$ cells. Thus, while some aspects of Reddy's method could be considered high throughput, his method is still quite limited in that it requires a particular type of plasma cell (BMPCs) that are isolated from the bone marrow of a euthanized animal.

Kodituwakku et al (Imm. Cell Biol. 2003 81: 163-170) reviewed the state of the art in methods for isolating antigen-specific B cells, e.g., by panning and other similar techniques. Kodituwakku concluded that, while several methods for isolating antigen-specific B cells exist, those methods provide very variable results and are plagued by non-specific binding, which in turn decreases the purity and enrichment of the desired cells in the isolated population.

In view of the above, there is still a need for high-throughput methods for generating antibodies.

SUMMARY

Provided herein, inter alia, is a method for producing an enriched population of antigen-specific plasma cells. In some embodiments, the method may comprise: (a) obtaining a sample of cells from an animal that has been immunized by an antigen, wherein the sample comprises B cells; (b) enriching for a population of antigen-specific B cells that comprise cell surface antibodies that are specific for the antigen by: i. contacting at least $10^5$ of the cells in said sample, en masse, with the antigen or a portion thereof; and ii. isolating cells that bind to the antigen or portion thereof; and (c) activating the enriched B cells, en masse, in the presence of the antigen or portion thereof to produce the enriched population of antigen-specific plasma cells.

Depending on how the method is implemented, the method can have certain advantages over conventional methods. For instance, as noted above, most methods for isolating antigen-specific B cells result in a population of cells that contains a significant amount of contaminating cells that non-specifically bind to the substrate. The activating step of the method described herein, only activates B cells that have surface-tethered antibodies which are bound to the antigen. This method provides two effects, firstly, the activating step causes only those B cells that are specifically bound to the antigen to proliferate, thereby increasing the relative concentration of those cells relative to the cells that are non-specifically bound to the support. Secondly, the activating step of the method causes expression of heavy and light chain mRNA to be induced only in those B cells that are specifically bound to the antigen. In other words, the additional activation step allows one to selectively stimulate memory B-cell to differentiate and become plasmablasts and plasma cells, which are rapidly dividing and expressing larger amounts of antibody.

On a per cell basis, the enrichment and activation steps, in combination, increase the total number of antigen-specific cells (i.e., the total number of cells that produce antibodies that bind to the antigen) and, in addition, increases the relative concentration of antigen-specific cells relative to other cells. The inventors' have found that up to 25-50% of the collected cells are antigen-specific and, as such, the enrichment may be well over 100-fold in many cases. As such, the collected cells can be screened (e.g., using conventional hybridoma methods) much more efficiently than other populations of cells, e.g., splenocytes or the like. Further, the enrichment and activation steps, in combination, may activate B cells that might not otherwise be activated in vivo (the reasons for which are unknown) thereby increasing the diversity of the pool of antibodies available for analysis. Finally, the enrichment and activation steps, in combination, cause "rare" antigen-specific B cells (e.g., B cells that encode antibodies that are unrelated by lineage to other antibodies being produced by the population) to proliferate, thereby increasing the probability that those cells (or sequences produced by the same) are identified when the cell population (or a collection of sequences obtained from the same) is screened.

Moreover, because the cells are employed en masse in the present method, the method is highly scalable and can be tailored, without additional effort, to produce as many different antigen-specific plasma cells as desired. For example, in some cases, a representative portion of the full antigenic response of an animal can be surveyed and thousands, if not tens of thousands, of hybridomas or sequences that encode antigen-specific antibodies can be obtained without additional effort. The ability to screen a significant portion of the full antigenic response of an animal also allows one to identify "rare" antibodies (e.g., antibodies that are not very abundantly expressed in the context of an otherwise strong immune response) and to perform further analysis on the antigenic response, such as lineage analysis or an analysis of the abundance of different antibody sequences. Lineage analysis requires sequence information for as many antibodies as possible and is useful because, once a candidate antibody that has desirable activity (e.g., a potential therapeutic or diagnostic activity) has been identified, then analysis of the lineage of that antibody can provide an insight into the structure of the antibody and allows one to identify amino acid residues that can be substituted (see, e.g., Yu et al, PLoS ONE, 2010 5: e9072). This, in turn, provides a way that second generation antibodies can be created in a targeted manner. Further, the magnitude of an immune response varies greatly from animal to animal and epitope to epitope and, in some cases, the titer of antibody to a particular epitope may be extremely low. The present method, because it applies an en masse approach, accommodates the unpredictability of an animal's immune response and facilitates the identification of rare antibodies because the entire immune response can effectively be screened in a single experiment.

These advantages are, in practice, impossible to achieve using the Lightwood method described above because Lightwood's methods require aliquoting a relatively small number of antibody-producing cells into each well of a microtiter plate in the hope that some of the wells receive no more than a single antigen-specific B-cell that becomes activated. Lightwood's method is limited by: a) Poisson distribution, meaning that there will always be wells that contain no antigen-specific B cells in addition to wells that contain too many antigen-specific B cells, making the method inefficient; b) lack of scalability in that the method requires an impractical amount of work (e.g., potentially hundreds or thousands of microtiter plates, assays and PCR reactions) to survey the entire immune system of an animal; and c) the lack of an efficient way to accommodate the unpredictability of an animal's immune response. The lack of an efficient way to accommodate the unpredictability of an animal's immune response means that, even under the best of conditions, practice of Lightwood's method requires doing the same experiment several times using several different dilutions of cells in order to obtain a dilution that potentially works, and then performing the method.

In addition to the above, the enrichment and activation steps also activates antibody expression in each of the activated B cells. This, in turn, vastly increases the amount of mRNA encoding antigen-specific antibodies in the resultant cell population. The additional activation step is particularly relevant for high throughput embodiments that involve sequencing the heavy and light chain cDNAs of the collected cells because, after enrichment, the enriched cells are still highly impure. The "noise" is generated by B cells that are non-specifically captured on the support or not washed away. These cells, which are mostly plasma cells, express several-fold more antibody than antigen-specific memory B cells. Therefore, without activation, the VH and VL sequences from the contaminating cells are often more abundant than the sequences for the antigen-specific antibodies. Therefore, sequencing the VH and VL cDNAs from a population that has been enriched but not activated (after bead purification for example), generates a data set that is predominantly composed of sequences for antibodies that are not antigen-specific. In contrast, sequencing the VH and VL cDNAs from a population that has been enriched and activated, generates a data set that is predominantly composed of sequences for antibodies that are antigen-specific.

As will be described in much greater detail below, the population of cells made by the present method may be fused with a suitable fusion partner to make hybridomas (which may be screened by hybridoma) or in some embodiments, cDNAs encoding the VH and VLs may be sequenced from those cells.

In hybridoma embodiments, the collected cells may fused with a suitable fusion partner to make hybridomas, and the hybridomas may be screened using any convenient method (e.g., ELISA) to identify a hybridoma that produces an antigen-specific antibody. In these embodiments, performing the enrichment and activation steps vastly decreases the number of clones to be screened (by over 10-fold in some instances), and, at the same time increasing the number of cells being input into the fusion step. Additionally, because the "rare" B cells have been amplified in the previous steps, there is a higher chance those cells will be represented in the hybridoma population. Specifically, the inventors found that "rare" antibodies, i.e., antibodies that are at low abundance would not otherwise be sampled from a B cell population (i.e., B cells obtained directly from an animal, without enrichment or activation) without an exhaustive sequencing effort or an exhaustive screen of hybridomas made from those cells, appear to be at an increased concentration relative to other cells in the enriched and activated B cells. As such, such rare antibodies have a higher chance of being identified by sequencing the heavy and light chains of an enriched and expanded B cell population, or by screening hybridomas made from those cells. Finally, immortalizing the collected B cells allows one to produce as much antibody as necessary without having to clone, sequence and validate in transient assay. This can save a significant amount of time and minimize overall handling in a production context.

In sequencing embodiments, the most abundant sequences (e.g., those that have a read count above a threshold, e.g., a threshold in the range of 5-10 sequence reads) can be readily identified. These sequences are more likely to be antigen-specific and, as such, the present method allows the rapid identification of hundreds, if not thousands, of antigen-specific VH and VL sequences without implementing a labor-intensive screening effort. As will be described in greater detail below, the sequences can be analyzed by tanglegram analysis to identify pairs of VH and VL sequences that can be expressed in a cell and tested. In addition, because multiple sequence reads are obtained for each VH or VL, sequencing errors can be corrected using bioinformatic methods.

Moreover, the inventors unexpectedly found that if enrichment and activation are performed the heavy and light chain sequences obtained by sequencing the population of activated cells are sometimes polarized and in certain cases can be paired by their relative abundance. In the inventor's experience, the heavy and light chain sequences obtained from B cells (i.e., B cells obtained directly from an animal, without enrichment or activation) are not as polarized and cannot be paired by their abundance. This allows one to identify antibodies by: enriching for a population of memory B cells by affinity to an antigen, activating those cells, collecting the cells (without any screening of culture supernatant to identify which cells produce antigen-specific antibodies), sequencing the heavy and light chains separately, and identifying and pairing heavy and light chain sequences together by their relative abundance to produce antibodies that bind to the antigen. This method, which can be done using a sample that in many cases can be very easy to obtain removes a significant bottleneck from the conventional methods.

In addition, the enrichment step of the method provides a means by which antigens can be multiplexed and "application-specific" antibodies can be produced. In multiplexing embodiments, an animal may be immunized with multiple antigens, and antigen-specific cells for each of a plurality of antigens may be enriched separately from one another. The antigen-specific cells can then be activated and collected separately from one another, as summarized above, to provide a plurality of populations of cells, each specific for a different antigen. "Application-specific" antibodies, i.e., antibodies that are selected for a particular use, e.g., FACS, immunoprecipitation, immunohistochemistry, therapeutics, etc.) can be produced by tailoring the enrichment step to favor cells that produce a particular type of antibody (e.g., antibodies that bind to one antigen but not another, antibodies that recognize cells, antibodies that bind only under certain conditions, or antibodies that bind to an antigen in fixed tissue section, etc.).

These and other advantages may be may be apparent in light of the description that follows below.

BRIEF DESCRIPTION OF THE DRAWINGS

The skilled artisan will understand that the drawings, described below, are for illustration purposes only. The drawings are not intended to limit the scope of the present teachings in any way.

FIG. 7A: overlap between total PBMC and affinity selected/proliferated VH sequences. FIG. 7B: Unique VH sequences only found in affinity selected/proliferated dataset.

DEFINITIONS

Figure 1:
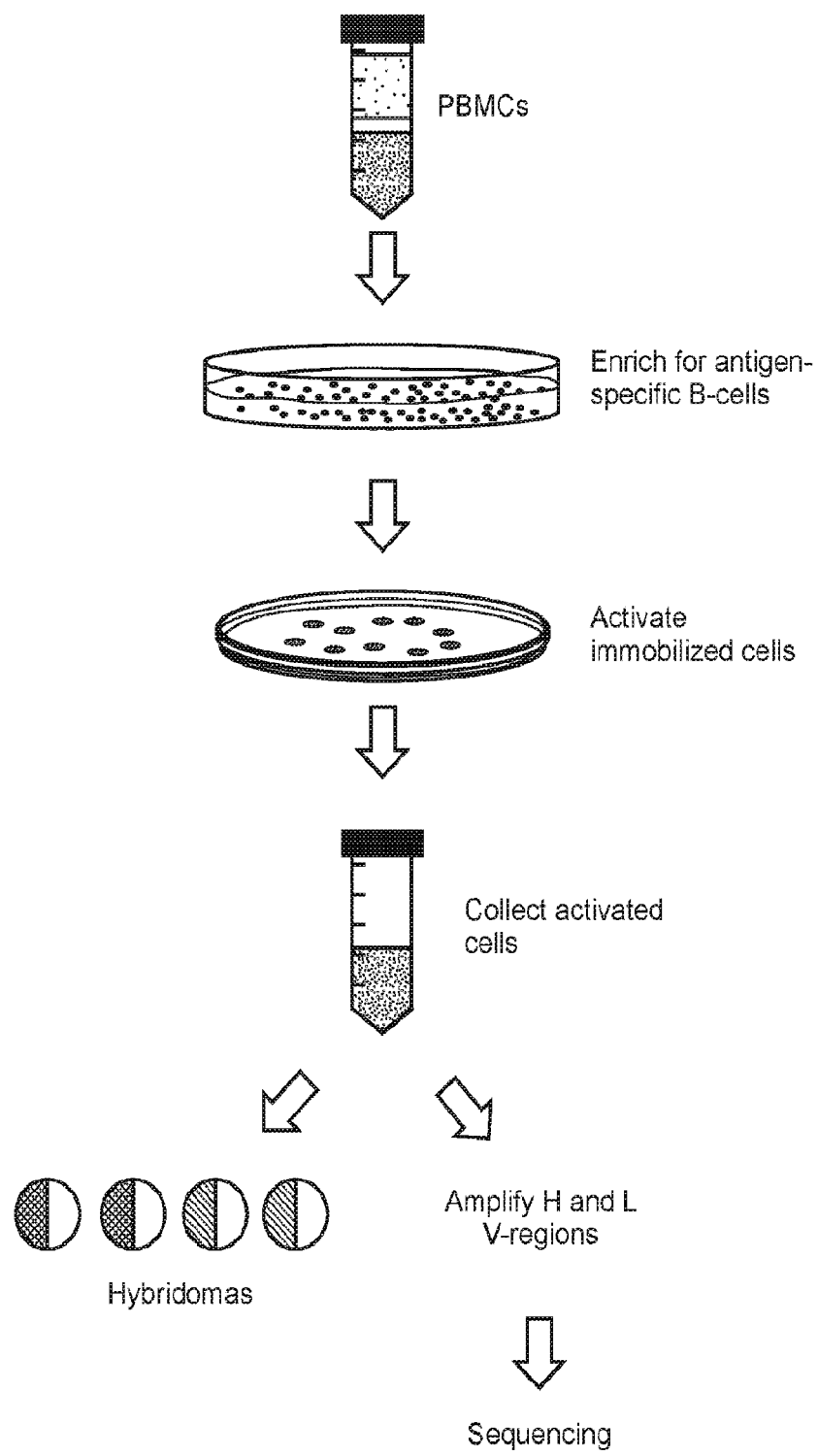
FIG. 1 schematically illustrates some of the general principles of the present method.

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a framework region" includes reference to one or more framework regions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "plurality" refers to more than 1, for example more than 2, more than about 5, more than about 10, more than about 20, more than about 50, more than about 100, more than about 200, more than about 500, more than about 1000, more than about 2000, more than about 5000, more than about 10,000, more than about 20,000, more than about 50,000, more than about 100,000, usually no more than about 200,000. A "population" contains a plurality of items.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the NH$_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed., 1984, and Hunkapiller and Hood, Nature, 323, 15-16, 1986).

An immunoglobulin light or heavy chain variable region consists of a framework region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

By "variable region of an immunoglobulin chain" or an "immunoglobulin chain variable region" is a polypeptide comprising at least a portion of the variable domain of a heavy (i.e., the VH domain) or a light chain (i.e., the VL domain) of an immunoglobulin, where the portion of the VL and the VH domains form an antigen binding domain of an immunoglobulin. Thus, the variable region of an immunoglobulin includes three CDRs flanked by either or both of FR1 and FR4 (e.g., FR1, CDR1, FR2, CDR2, FR3, CDR3, FR4). In some embodiments, the immunoglobulin chain variable region is the region on one of either the heavy or the light chain which, when combined with the immunoglobulin chain variable region of the other chain (i.e., the light or the heavy chain) of immunoglobulin, forms the antigen binding domain.

By "antigen binding domain" is meant the region of a single heavy chain assembled with a single light chain in an immunoglobulin, which has the specific binding activity of the intact antibody for its specific antigen. Thus, an intact IgG immunoglobulin, which comprises two heavy chains and two light chains, has two antigen binding domains.

The term "natural" antibody refers to an antibody in which the heavy and light chains of the antibody have been made and paired by the immune system of a multi-cellular organism. Spleen, lymph nodes, bone marrow and blood are examples of tissues that contain cells that produce natural antibodies. For example, the antibodies produced by B cells isolated from a first animal immunized with an antigen are natural antibodies. Natural antibodies contain naturally-paired heavy and light chains.

The term "naturally paired" refers to heavy and light chain sequences that have been paired by the immune system of a multi-cellular organism.

The term "mixture", as used herein, refers to a combination of elements, e.g., cells, that are interspersed and not in any particular order. A mixture is homogeneous and not spatially separated into its different constituents. Examples of mixtures of elements include a number of different cells that are present in the same aqueous solution in a spatially undressed manner.

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present, and/or determining whether it is present or absent.

The term "enriched" is intended to refer to component of a composition (e.g., a particular type of cells) that is more concentrated (e.g., at least 2×, at least 5×, at least 10×, at least 50×, at least 100×, at least 500×, at least 1,000×), relative to other components in the sample (e.g., other cells) than prior to enrichment. In some cases, something that is enriched may represent a significant percent (e.g., greater than 2%, greater than 5%, greater than 10%, greater than 20%, greater than 50%, or more, usually up to about 90%-100%) of the sample in which it resides.

The term "enriching" is intended to any way by which antigen-specific cells can be obtained from a larger population of B cells. As will be described in greater detail below, enriching may be done by panning, using bead or cell sorting, for example.

The term "obtaining" in the context of obtaining an element, e.g., cells or sequences, is intended to include receiving the element as well as physically producing the element.

The term "peripheral blood mononucleated cells" or "PBMCs" refers to blood cells that have a single approximately round nucleus (as opposed to a lobed nucleus) and includes lymphocytes (T cells, B cells and NK cells), monocytes and macrophage. PBMCs can be enriched from whole blood using a ficoll gradient.

The term "cell surface antibody" refers to an antibody that is tethered to the surface of a B cell. B cells that have cell surface antibodies include memory B cells and naïve B cells. Such an antibody may be referred to as the "B cell receptor" in some publications.

The term "specific binding" refers to the ability of an antibody to preferentially bind to a particular antigen that is present in a homogeneous mixture of different molecules. In certain embodiments, a specific binding interaction will discriminate between desirable and undesirable molecules in a sample, in some embodiments more than about 10 to 100-fold or more (e.g., more than about 1000- or 10,000-fold).

In certain embodiments, the affinity between an antibody and an antigen when they are specifically bound in a capture agent/analyte complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

The term "antigen-specific B cells" refers to memory B cells that have an antibody that specifically binds to an antigen on their surface, as well as progenitors thereof.

A cell is "derived from" a host if the cell, or the progeny thereof, was obtained from the host. The progeny of a progenitor cell are derived from the progenitor cell.

The term "support comprising the antigen" comprises any type of support (e.g., a solid or semi-solid support, including plates and beads) that contains an antigen, or a portion thereof, immobilized thereon. An antigen may be immobilized on a support directly or indirectly, e.g., via a linker, via a biotin-streptavidin interactin or via a cell, for example. Methods that enrich for antigen-specific B cells by panning or using beads make use of such a support.

The term "panning" is used to refer to a method by which B cells are applied to a container (e.g., a plate) that has one or more surfaces that are coated in an antigen or portion thereof. Unbound cells can be removed by washing the surface after the cells are applied to it.

The term "bead-based enrichment" is used to refer to a method by which B cells are mixed with beads, e.g., magnetic beads, that are linked to an antigen or portion thereof.

The term "cell sorting" is used to refer to a method by which B cells are mixed a detectable antigen (e.g., a fluorescently detectable antigen) in solution. In cell sorting methods, cells that are bound to the antigen are sorted from the unbound cells. Fluorescence-activated cell sorting (FACS) is an example of a cell sorting method.

The term "antigen, or a portion thereof" refers to an antigen that was used for immunization, or part of the same (e.g., a peptide of 5-20 amino acids in length).

The term "complex immunogen" is intended to refer to an immunogen that contains a plurality of antigens. A complex immunogen can be composed of a plurality of different antigens that have been separately made and then mixed together, or they may be naturally complex (e.g., as is the case when one uses an entire cell or a fraction thereof) in an immunization.

The term "activating" is referred to the stimulation of B cells to a) proliferate and b) differentiate into plasmablasts and/or plasma cells and c) secrete antibodies. B cell activation can be done by contacting the B cells with antigen, T cells expressing CD40L and cytokines, although other methods are known (see, e.g., Wykes, Imm. Cell. Biol. 2003 81: 328-331).

The term "activated B cells" refers to a cell population that comprises the progeny of a B cell that was activated. As noted above, activation causes B cells to proliferate, and the progeny of such cells are referred to herein as activated B cells.

The term "collecting" refers to the act of separating the cells that in the culture medium from the a substrate. Collecting may be done by pipetting or by decanting, for example.

The term "immunized by an antigen" and grammatical equivalents there of (e.g., "immunized animal") is intended to refer to any animal (humans, rabbits, mice, rats, sheep, cows, chickens, humans, camels) that is mounting an immune response an antigen. An animal may be exposed to a foreign antigen via exposure to an infectious agent, a vaccination, or by administrating an antigen and adjuvant (e.g., by injection), for example. The term "immunized by an antigen" is also intended to include animals that are mounting an immune response against a "self" antigen, i.e., have an autoimmune disease.

The term "en masse" refers to the addition of a sample to a container as a single unit, without sub-fractionating or sub-dividing the sample beforehand or afterwards. For example, aliquoting portions of a sample into individual wells of a multi-well plate is not an en masse action. Aliquoting portions of a sample into the same well of a multi-well plate (i.e., making multiple transfers from one container to another using the same pipettor) is an en masse action. At least $10^5$, at least $10^6$ or at least $10^7$ cells may be used en masse.

The terms "ranking" and "ranked order of abundance" refer to the order of sequences when they are listed by their abundance, i.e., with the most abundant sequence first, the second most abundant sequence next, and the third most abundant sequence next, and so on. In certain cases, sequences may be ranked by making a frequency distribution, and then ordering the sequences by their frequency.

The term "corresponding rank" or "correspondingly ranked" refer to two sequences that have the same positions in two ranks. For example, the first, second and third positions in a first rank correspond to the first, second and third positions in a second rank, respectively. As will be described in greater detail below, ambiguities in a ranking (e.g., if two sequences are expressed at a similar abundance) can may be resolved by analyzing the lineage of those sequences.

As used herein, the term "lineage-related antibodies" and "antibodies that related by lineage" as well as grammatically-equivalent variants there of, are antibodies that are produced by cells that share a common B cell ancestor. Antibodies that are related by lineage bind to the same epitope of an antigen and are typically very similar in sequence, particularly in their L3 and H3 CDRs. Both the H3 and L3 CDRs of lineage-related antibodies can have an identical length and a near identical sequence (i.e., differ by up to 5, i.e., 0, 1, 2, 3, 4 or 5 residues). In certain cases, the B cell ancestor contains a genome having a rearranged light chain VJC region and a rearranged heavy chain VDJC region, and produces an antibody that has not yet undergone affinity maturation. "Naïve" or "virgin" B cells present in spleen tissue, are exemplary B cell common ancestors.

Related antibodies are related via a common antibody ancestor, e.g., the antibody produced in the naïve B cell ancestor. The term "lineage related antibodies" is not intended to describe a group of antibodies that are not produced by cells that arise from the same ancestor B-cell. A "lineage group" contains a group of antibodies that are related to one another by lineage.

As used herein, the term "at least the CDR3s" or "at least the CDR3 sequences" refers to only CDR3 sequences, CDR3 sequences in conjunction with CDR1 and/or CDR2 sequences or a sequences of at least 50 contiguous amino acids of the variable domain, up to the entire length of the variable domain, where the sequence contains a CDR3 sequence.

As used herein, the terms "cladogram" and "lineage tree" refers to a diagram, resulting from a cladistic analysis, which depicts a hypothetical branching sequence of lineages leading to the individual species of interest. The points of branching within a cladogram are called nodes.

As used herein, the term "constructing a phylogenetic tree" refers to the computational act of making a phylogentic tree from sequences.

As used herein, the term "lineage" refers to a theoretical line of descent.

As used herein, the term "lineage analysis" refers to the analysis of the theoretical line of descent of an antibody, which is usually done by analyzing a lineage tree.

As used herein, the term "sequence read" refers to a sequence of nucleotides determined by a sequencer, which determination is made, for example, by means of base-calling software associated with the technique.

As used herein, the term "clade" refers to a group of VH or VL sequences that are related by lineage, i.e., they are descents of a common ancestor.

As used herein, the term "antibody heavy and/or light chain sequences" refers to either the VH of an antibody, the VL chain of an antibody, or both the VH and VL chains of an antibody.

As used herein, the term "obtaining the amino acid sequences" refers to obtaining a file containing amino acid sequences. As is well known, a nucleic acid sequence can be translated into an amino acid sequence in silico.

As used herein, the term "most abundantly expressed", with reference to a protein sequence, refers to a protein sequence that is most abundant in a sample. The abundance of a protein can be determined by, e.g., counting sequence reads encoding that protein. The protein with the most sequence reads is the most abundant protein.

As used herein, the term "sequence comparison" refers to a method for comparing a query sequence with a database of sequences, and identify library sequences that resemble the query sequence above a certain threshold. BLAST (Altschul et al Journal of Molecular Biology 1990 215: 403-10) and FASTA (Lipman et al Science 1985 227: 1435-41) are examples of algorithms that can be used for sequence comparison, and many others are available.

Figure 3:
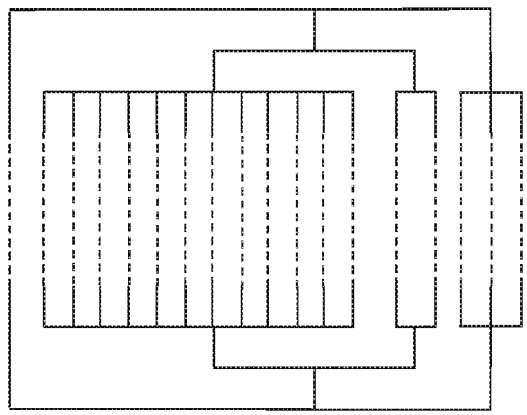
FIG. 3 schematically illustrates how lineage trees can be aligned in a tanglegram.
Figure 3:
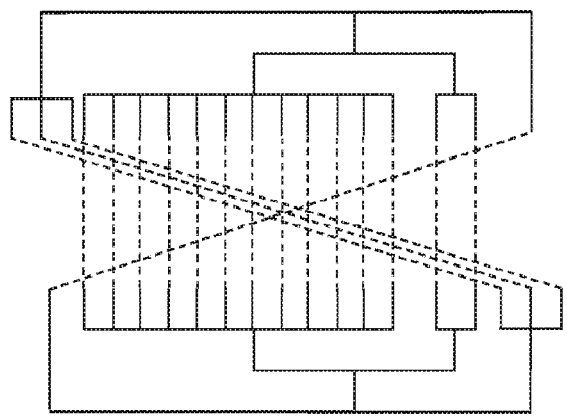

As used herein, the term "tanglegram" refers to a pair of lineage trees in which leaves are aligned with one another in a way that minimizes "crossovers" in the pairings (see FIG. 3). Every branch of a lineage tree is rotatable around a node and, in making a tanglegram, the branches are been rotated around their nodes to provide the best match between the leaves, where the best match minimizes the number of crossovers between the matched leaves. Tanglegrams have been widely used in biology to compare evolutionary histories of things that are related to one another, e.g., to analyze the molecular evolution of host and parasite species, or to analyze genes of species in the same geographical area. Tanglegrams are described in great detail in Scornavacca et al (Bioinformatics 2011 27: 248-256), Venkatachalam et al (IEEE/ACM Trans Comput Biol Bioinform. 2010 7: 588-97) and Lozano (IEEE/ACM Trans Comput Biol Bioinform. 2008 5:503-13). FIG. 3 shows an example of how tanglegram analysis can align two simple lineage trees. In this example, the crossovers are completely eliminated.

Figure 4:
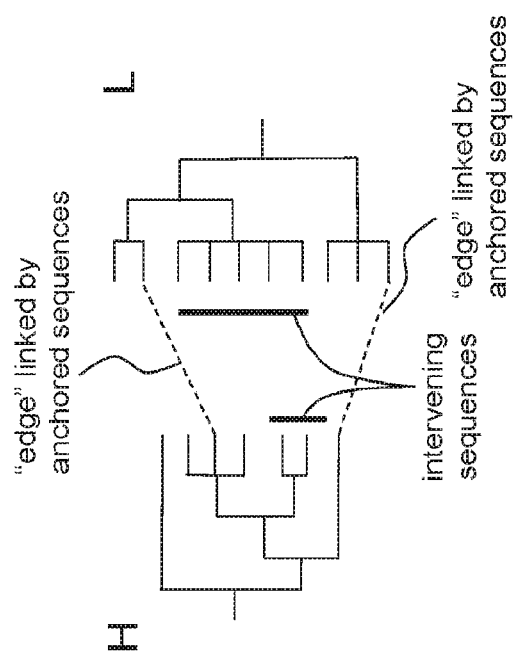
FIG. 4 schematically illustrates how intervening VH and VL sequences in an anchored tanglegram can be paired.
Figure 8:
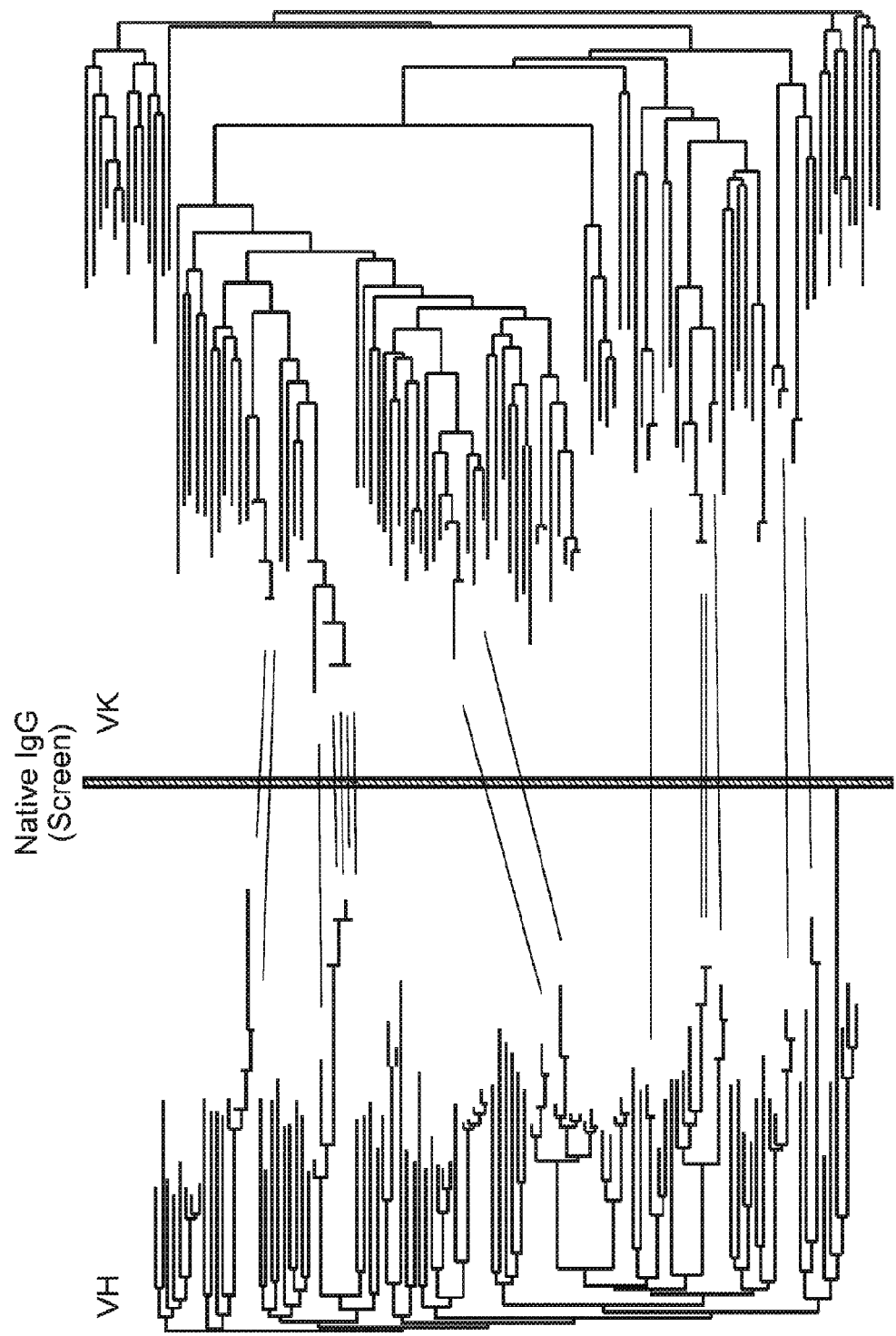
FIG. 8 shows an example of an anchored tanglegram.

Tanglegrams can be "anchored" using leaves that are known to pair with one another. In these embodiments, the branches are rotated around their nodes until there is a minimal number of cross-overs (e.g., no crossovers) between the anchored sequences. After the trees have been "aligned" by tanglegram analysis, the leaves that are known to pair can be connected by an edge (as indicated by lines drawn between the leaves of the phylogenetic trees illustrated in FIGS. 4 and 8, for example). If the leaves that are known to pair are connected by an edge, the intervening leaves, in theory, can pair with one another as long as they do not create a cross-over event with an edge or one another. FIGS. 4 and 8 show examples of an anchored tanglegram in which the intervening sequences (i.e., the sequences that are not linked by an edge) can be paired with one another as long as the pairing does not create a cross-over with an edge or one another.

As used herein, the term "aligned", in the context of a tanglegram, refers to two sequences that lie across from one another in a tanglegram, where "across from one another" means that they can be paired without making a cross-over with a known edge. One sequence in one lineage tree may be aligned with more than sequence in another tree. The tanglegram shown in FIG. 8 shows an example of a tanglegram of a VH and VL sequences are aligned.

As used herein, the term "inputting" is used to refer to any way of entering information into a computer. For example, in certain cases, inputting can involve selecting a sequence or a model that is already present on a computer system. In other cases, inputting can involve adding a sequence or a model to a computer system. Inputting can be done using a user interface.

As used herein, the term "executing" is used to refer to an action that a user takes to initiate a program.

DETAILED DESCRIPTION OF EXEMPLARY EMBODIMENTS

One implementation of the present method is schematically illustrated in FIG. 1. With reference to FIG. 1, certain embodiments of the method may comprise: obtaining a population of cells that comprise B cells from an animal that has been immunized by an antigen. In the example shown in FIG. 1, peripheral blood mononucleated cells (PBMCs) are obtained. However, other sources of B cells (e.g., spleen, lymph nodes and bone marrow) may be used instead. Next, the method comprises enriching for a population of antigen-specific B cells that comprise cell surface antibodies that are specific for the antigen. In general terms, this step of the method involves contacting at least $10^5$ of the cells in the sample, en masse, with the antigen or a portion thereof and isolating cells that bind to the antigen or portion thereof. This step may be done by panning (as shown in FIG. 1), although any other suitable method, e.g., bead-based enrichment method, or by cell sorting (e.g., FACS), may be used instead. For example, in embodiments that use panning or beads, this step of the method may be done by i. contacting at least $10^5$ of the cells in the sample, en masse, with a support (e.g., a container or population of beads) comprising the antigen, or a portion thereof, under conditions by which the antigen-specific B cells bind to the antigen or portion thereof; and ii. washing the support to remove unbound cells. In embodiments that use cell sorting, this step of the method may be done by: i. contacting at least $10^5$ of the cells in the sample, en masse, with the antigen, or a portion thereof under conditions by which the antigen-specific B cells bind to the antigen or portion thereof; and ii. sorting cells that bind to the labeled antigen or portion thereof.

Next, the enriched B cells are activated, en masse, in the presence of the antigen or portion thereof. In these embodiments, the antigen or portion thereof may be added to culture medium in addition to the other necessary ingredients for activating the cells. Finally, the method may comprise collecting the activated cells, e.g., by decanting or pipetting the cells.

As will be described in greater detail below, the collected cells may be used in a variety of different ways without the need for testing the culture medium of the activated cells to determine if the cells secrete an antibody that binds to the antigen or portion thereof.

In some embodiments, the enriching step of the method comprises i. contacting a plurality of cells from the sample (e.g., at least $10^5$, at least $10^6$ or at least $10^7$ cells), en masse, with a support comprising the antigen, or a portion thereof, under conditions by which the antigen-specific B cells bind to the antigen or portion thereof; and ii. washing the support to remove unbound cells. The enrichment step may done using any suitable enrichment method that employs a support, e.g., an antigen-coated solid support (such as a Petri dish or the like) or antigen-coated beads (e.g. magnetic beads or streptavidin coated beads). These methods may sometimes be referred to as "panning" or "bead-based" enrichment and examples of such methods are described are described in Lightwood supra, Kodituwakku, supra, and U.S. Pat. No. 7,790,414 which are incorporated by reference. In alternative embodiments, antigen-specific B cells may be obtained by FACS (see, e.g., Weitkamp et al 2003 J. of Imm. Methods 275, 223-237 and US20130017555). If FACS is used, the sorted cells may be all combined into a single wells, not separated into different wells. In sorting embodiments, the cells may be labeled to detect the presence of other cell surface markers, thereby allowing specific cell types, e.g., memory cells, to be enriched.

In performing this step of the method, the B cells may sometimes be allowed to contact a support (e.g. a plate or beads if beads are being used) that has been coated in antigen or portion thereof for sufficient time to allow binding. B cells that do not bind to the support may then be removed, leaving those B cells which are bound to the support. In some embodiment, the antigen is the same as that used to immunize the animal, or a portion thereof. As will be described in greater below, the antigen on the substrate may be presented to the B cells in a way that selects B cells that express application-specific antibodies (i.e., antibodies that can be used for FACS, immunohistochemistry, western blotting, therapeutics, etc.). In certain embodiments, the B cells may be depleted for cells that non-specifically bind to other antigens. In these embodiments, the cells may be bound to a first substrate to remove cells that non-specifically bind to another antigen, prior to binding to the support containing the antigen of interest. This step can be used to remove cells that bind to antigens that are similar to the antigen of interest, or other sources of potential contamination. In other cases, a second antigen can be added to the solution during the enrichment step, where the second antigen blocks non-specific binding of some cells to the antigen on the substrate.

Once the B cells have been in contact with the substrate for sufficient time to allow binding, the mixture is then washed with a medium that facilitates removal of the non-adhering cells from the substrate but which leaves cells that are bound to the support via antibodies that are on the surface of the B cells. Suitable media will be known to those skilled in the art or can be readily determined empirically by those skilled in the art. Any culture medium for example Roswell Park Memorial Institute medium (RPMI) or Dulbecco's Modified Eagle Medium (DMEM) may be used. In some cases, a number of washes may be employed to remove the non-adherent cells, e.g., 5 or 10 or more washes.

The enriching may be done in any suitable container. The container used may be chosen to accommodate the volume of cells (e.g., PBMCs) used in the method. In some cases, $10^4$ to $10^7$ cells (e.g., $10^5$ to $10^7$ or more cells) in a volume of 0.5 ml to 50 mls (e.g., 1 ml to 10 ml) are deposited into a vessel that contains the support. In some embodiments, the antigen or portion thereof will saturate the surface of the container. Those skilled in the art will be readily able to adjust the parameters of the enrichment step to optimize the number and type of B cells that are retained on the substrate. Parameters which may be adjusted include the volume added to the substrate, the surface area of the substrate, the concentration or amount of antigen bound to the substrate; the concentration or amount of B cells added to the container; the source of B cells (e.g. if the B cells are from a low responder then more B cells could be used); the number of washes to remove the non-adhering cells; the wash solution, etc. In contrast to some other methods, this method does not require depositing single cells into multiple containers, nor carefully titrating the number of B cells added to a container in the expectation that each container will contain a relatively small number, e.g., under 5 (e.g., one, two, three, four or five) antigen-specific B cells. Rather, in the present method as many B cells as desired can be added to the substrate, without titrating the amount of antigen-specific B cells are being added to the container.

Alternatively, the antigen or portion thereof may be coated onto beads. The use of beads to select for cells which bind to an antigen of interest is well documented in the art. Briefly, for example, the antigen or portion thereof may be bound to magnetic beads. The B cells are then mixed with the magnetic beads and those B cells which bind to the antigen or portion thereof will bind to the magnetic beads via the capturing agent. The B cells which bind to the magnetic beads may then be obtained by magnetic separation. The use of magnetic beads is described in Lagerkvist et al. (BioTechniques 1995 18:862-869).

As noted above, cell sorting (e.g., FACS) may be used in some implementations of the method. In these implementations, the antigen or portion thereof may be fluorescently labelled to facilitate the FACS sorting of the B cells. If cell sorting is used, the majority, e.g., at least 50%, at least 70% or at least 90% of the enriched cells, e.g., at least 1,000, at least 5,000, at least 10,000, at least 50,000 or at least 100,000 cells may be activated, en masse, in the next step of the method.

When enriching for those cells that produce an antibody that specifically binds to the antigen of interest, it may be desirable to ensure that B cells that non-specifically bind (e.g. to the support or to cells not expressing the antigen) are not selected. In these embodiments, the B cells may be first exposed to the container and/or support to which no antigen or portion thereof has been bound and then disposing of those B cells which non-specifically bind to the container. Similarly, if beads are used, then prior to incubating the B cells with antigen-coated beads the B cells may first be incubated with uncoated beads and the cells that bind to the uncoated beads may then be removed. Alternatively, cells that non-specifically bind to the antigen or portion thereof can be removed after to the cells after they have been enriched.

As would be apparent, the cells used in the present method may be obtained from various sources. For example, the cells could be obtained from the spleen, lymph nodes bone marrow or peripheral blood of an animal that has either been immunized with an antigen, or that has developed an immune response to an antigen as a result of disease. Animals may be immunized with a selected antigen using any of the techniques well known in the art suitable for generating an immune response (see Handbook of Experimental Immunology, D. M. Weir (ed.), Vol 4, Blackwell Scientific Publishers, Oxford, England, 1986). Many warmblooded animals, such as humans, rabbits, mice, rats, sheep, cows, chickens, humans, camels or pigs may be immunized. In some embodiments, the animal may have an autoimmune disease, or may have developed resistance to or has recovered from a disease (e.g., cancer). In some embodiments, antibody-producing cells may also be obtained from a subject that has generated the cells during the course of a selected disease or condition. For instance, antibody-producing cells from a human with a disease of unknown cause, such as rheumatoid arthritis, may be obtained and used in an effort to identify antibodies which have an effect on the disease process or which may lead to identification of an etiological agent or body component that is involved in the cause of the disease. Similarly, antibody-producing cells may be obtained from subjects with disease due to known etiological agents such as malaria or AIDS. These antibody-producing cells may be derived from the blood, lymph nodes or bone marrow, as well as from other diseased or normal tissues. Cells obtained from humans that have been exposed to an antigen, e.g., vaccinated, may be used.

In some embodiments, the animal may be been immunized with the antigen, e.g., multiple times in the presence of an adjuvant. In these embodiments, suitable antigens are numerous and include soluble and solubilized proteins, including extracellularly-exposed fragments membrane proteins In particular embodiments, the animal may be immunized with a complex immunogen that contains multiple antigens (e.g., at least 2, at least 5, at least 10, at least 50, at least 100, at least 500 or at least 1,000, up to 5,000 or more antigens).

If PBMCs are used, they may be enriched from blood that has been treated with an anticoagulant such as heparin or EDTA. PBMCs may be isolated from whole blood by lympholyte density centrifugation (Biozol; #CL5120) or using a Ficoll density gradient (Sigma-Aldrich, catalog number: 10771; MP Biomedicals, catalog number: 091692254). Methods for isolating PBMCs are well known (see, e.g., Panda, Bio-protocol 2013 3: e323) and in certain cases may include the following steps: collect venous blood sample and mix with heparin, layer the blood on the top of Ficoll Histopaque, centrifuge 30 min at 100×g in 4° C. in a swing-out bucket; remove the cells in the interphase between histopaque and medium, and then wash the cells, e.g., with PBS. In many species, the approximate yield of cells from 4 ml of blood may vary between $10^5$-$10^8$.

After the antigen-specific B cells have been enriched, they are activated in the presence of the antigen or portion thereof. The B cells may be activated by any suitable method, e.g., by CD40 activation. In certain cases, the activating may be done by, e.g., by contacting the immobilized cells with a medium containing the antigen or portion thereof that also contains CD40-L (which may be on a T cell) and one or more cytokines and/or growth factors (see, e.g., Liebig et al, J Vis Exp. 2010 Mar. 5 37: 1734; van Kooten et al, J. Leukoc. Biol. 2000 67:2-17; Kondo et al, Clin Exp Immunol. 2009 155:249-56; WO 91/09115; WO 94/24164; Tsuchiyama L et al., Hum Antibodies. 1997 8:43-7; Imadome et al., Proc Natl Acad Sci. 2003 100:7836-40, among others).

In some embodiments, the activation step results in activation of at least 100 antigen specific B cells (e.g., at least 500 antigen specific B cells, at least 1,000 antigen specific B cells, at least 5,000 antigen specific B cells, at least 10,000 antigen specific B cells, at least 50,000 antigen specific B cells or at least 100,000 antigen specific B cells) in the same vessel, resulting in a culture medium that contains a mixture of at least $10^5$ activated B cells (e.g., at least $10^6$ activated B cells, at least $10^7$ activated B cells or at least $10^8$ activated B cells) that is made up of several clonal populations of B cells (e.g., at least 50 clonal populations of B cells, at least 100 clonal populations of B cells, at least 500 clonal populations of B cells, at least 1000 clonal populations of B cells, at least 5000 clonal populations of B cells, at least 10,000 clonal populations of B cells, at least 50,000 clonal populations of B cells or at least 100,000 clonal populations of B cells, etc.), and a highly complex mixture of antibodies. The next step of the method may be performed without testing the culture medium to determine if antigen-specific antibodies are being produced although, in some cases, one may want to optionally test the culture medium for antigen-specific antibodies before continuing.

After the B cells are activated and have proliferated, they are collected. As noted above, this may be done by pipetting or decanting the culture medium from the solid support, and placing the decanted material into a vessel. This step may be done en masse, too. The collected B cells may be used in a variety of applications as described below.

B Cell Fusion Embodiments

In some embodiments, the method may comprise fusing the activated cells with a fusion partner to produce a plurality of hybridomas and screening the hybridomas to identify a hybridoma that produces an antibody that binds to the antigen or portion thereof.

Figure 2:
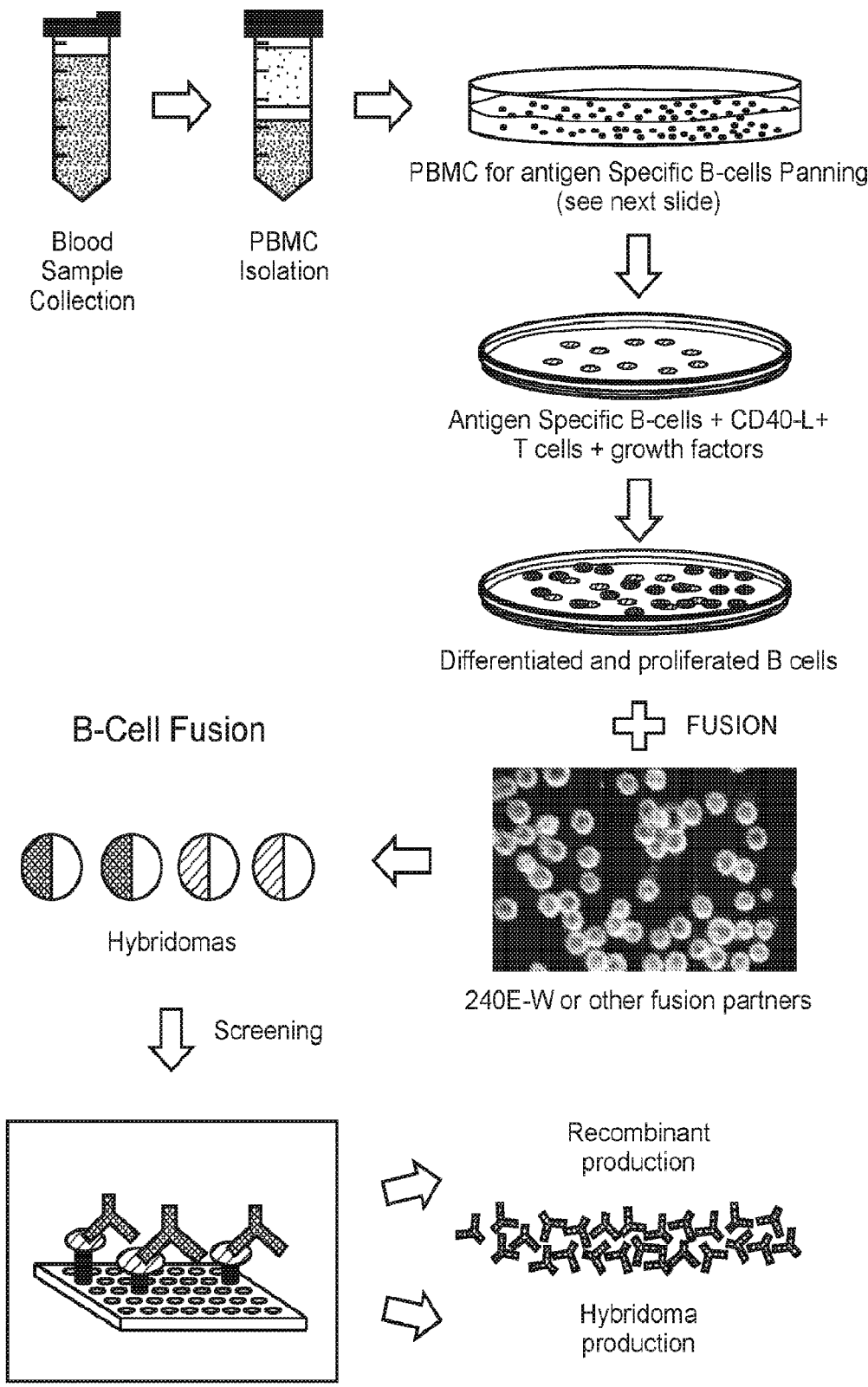
FIG. 2 schematically illustrates an embodiment in which the activated B cells are fused with a fusion partner to make hybridomas.

In these embodiments, the collected cells may be fused with a suitable immortal cell (e.g., NIH 3T3, DT-40 or 240E cell, etc.; Spieker-Polet et al, Proc. Natl. Acad. Sci. 92: 9348-9352, 1995) to produce hybridomas. In these embodiments, at least $10^5$, at least $10^6$ or at least $10^7$ of the collected B cells may be fused with a suitable fusion partner and deposited into wells, using any suitable method. Supernatants from the wells are screened for antibody secretion by enzyme-linked immunosorbent assay (ELISA) and positive clones secreting monoclonal antibodies specific for the antigen can be selected and expanded according to standard procedures (Harlow et al. *Antibodies: A Laboratory Manual*, First Edition (1988) Cold spring Harbor, N.Y.; and Spieker-Polet et al., supra). Suitable monoclonal antibodies may be further selected in the basis of binding activity, including its binding specificity, binding affinity, binding avidity, a blocking activity or any other activity that causes an effect (e.g. promoting or inhibiting a cellular phenotype, e.g., cell growth, cell proliferation, cell migration, cell viability (e.g., apoptotis), cell differentiation, cell adherence, cell shape changes (e.g., tubular cell formation), complement dependant cytotoxicity CDC, antibody-dependent cell-mediated cytotoxicity ADCC, receptor activation, gene expression changes, changes in post-translational modification (e.g., phosphorylation), changes in protein targeting (e.g., NFκB localization etc.), etc., or inhibition of receptor multimerization (e.g., dimer or trimerization) or receptor-ligand interactions). Antibody-encoding nucleic acids are isolated from hybridomas using standard molecular biology techniques such as polymerase chain reaction (PCR) or reverse transcription PCR (RT-PCR) (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.), and transferred to a different host to express recombinant antibodies. An example of this method is illustrated in FIG. 2.

Sequencing Embodiments

In some embodiments, the method may comprise making cDNA from the collected cells, and sequencing the cDNA to obtain a plurality of VH (heavy chain variable domain) sequences and a plurality of VL (light chain variable domain) sequences. In these embodiments, the method may further comprise selecting a VH and a VL sequence, and testing an antibody comprising the selected sequences to determine if the antibody binds to the antigen or portion thereof. In some embodiments and as will described in greater detail below, the heavy and light chain sequences may be selected by: i. obtaining a tanglegram of a plurality of the most abundant heavy and light chain sequences, wherein the tanglegram is anchored using heavy and light chains that are naturally paired with one another; ii. selecting a heavy chain sequence and a light chain sequence, wherein the selected heavy and light chain sequences are aligned with one another in the tanglegram; and iii. testing an antibody comprising the selected heavy and light chain sequences to determine if the antibody binds to the antigen or portion thereof.

In these embodiments, cDNAs encoding the antibodies produced by the collected cells may be sequenced. In certain embodiments, at least the cDNAs encoding the variable domains of the heavy and light chains are amplified. Strategies for performing RT-PCR to amplify sequences that encode antibodies for rabbits, mouse and humans, among others, are described in US20040067496, Kantor et al (Ann. N Y Acad. Sci. 1995 764: 224-7), Boekel et al (Immunity. 1997 7:357-68), Yamagami et al (Immunity 1999 11:309-16), Beerli et al (MAbs. 2010 2), Morbach et al (Mol. Immunol. 2008 45:3840-6), Kiippers et al (Methods Mol Biol. 2004 271: 225-238) and Seidl et al (Int. Immunol. 1997 9:689-702), which are incorporated by reference herein. Several strategies for cloning antibody sequences by PCR are known and may be readily adapted for use in the instant method (e.g., by using a CDR-specific primer in addition to a disclosed primer). Such strategies include those described by: LeBoeuf (Gene. 1989 82:371-7), Dattamajumdar (Immunogenetics. 1996 43:141-51), Kettleborough Eur. J. Immunol. 1993 23:206-11), Babcook (Proc. Natl. Acad. Sci. 1996 93: 7843-7848) and Williams (Cold Spring Harb. Symp. Quant. Biol. 1989 54:637-47) as well as many others. In certain cases, the second primer may be a mixture of different primers or degenerate primers, for example.

In some embodiments, the entire polynucleotide encoding a VH or VL sequence may be amplified using primers spanning the first and last codons of those regions. In certain cases, universal primers or degenerate primers may be used. Suitable tails may be added to the primers to facilitate sequencing. Amplification procedures using nested primers may also be used, where such nested primers are well known to one of skill in the art.

As would be apparent, the sequencing may be done using a next generation sequencing platform, e.g., Illumina's reversible terminator method, Roche's pyrosequencing method (454), Life Technologies' sequencing by ligation (the SOLiD platform), Life Technologies' Ion Torrent platform, of Pacific Biosciences SMRT platform, etc. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. In other embodiments, the sequencing may be done using nanopore sequencing (e.g. as described in Soni et al Clin Chem 53: 1996-2001 2007, or as described by Oxford Nanopore Technologies).

Depending on the read depth desired, the sequencing step may result in at least 5,000 heavy chain sequence reads (at least 10,000, at least 50,000, at least 100,000, at least 500,000, at least 1M, at least 5M, at least 10M, at least 50M or at least 100M heavy chain sequence reads) and at least 5,000 light chain sequence reads (at least 10,000, at least 50,000, at least 100,000, at least 500,000, at least 1M, at least 5M, at least 10M, at least 50M or at least 100M heavy chain sequence reads). In certain embodiments, each of the sequence read can cover the entire variable region of the heavy chain or light chain of an antibody. At this point, the heavy and light chain sequences are unpaired in the sense that one does not know which light chain sequence pairs with which heavy chain sequence.

As noted above, the heavy and light chains may be paired using tanglegram analysis. In these embodiments, the method may comprise making a lineage tree for the most abundant VH sequences and a lineage tree for the most abundant VL sequences and aligning the trees in a tanglegram. In some embodiments, the number of sequences that are selected for analysis may be chosen arbitrarily or, in certain embodiments, the number of sequences that are chosen for analysis may be represented by a certain number of sequence reads (e.g., at least 10, at least 50, at least 100, at least 500, at least 1,000, at least 2,000, at least 5,000 or at least 10,000 sequence reads). Either way, a number of the most abundant VH and VL sequences (e.g., up to 50, up to 100, up to 500, up to 1,000, up to 2,000, or up to 5,000 of the most abundant VH and VL sequences) are selected. After the most abundant VH and VL sequences are selected, a tanglegram is constructed, which general involves making separate lineage trees (one tree for the selected VH sequences and another tree for the selected VL sequences) and then making a tanglegram that is anchored by VH and VL that are known to pair with each another. As explained above, in these embodiments, the branches of the lineage trees are rotated around their nodes until there are a minimal number of cross-overs (e.g., no crossovers) between the anchored sequences. After the trees have been "aligned" by tanglegram analysis, the sequences that are known to be paired to each other can be connected by an edge, as shown in FIGS. 4 and 8. The intervening sequences can be paired with one another and tested as long as the pairing does not create a cross-over with an existing edge. This concept is illustrated in FIG. 4. The lineage analysis may be done using at least the CDR3 regions (e.g., only the CDR3 regions, all of the CDRs, or the entire variable region) encoded by the sequence reads, for example. In some cases, sequence abundance may be taken into consideration in selecting a VH sequence and a VL sequence for testing. For example, if there are three intervening VH sequences and three intervening VL sequences, then the most abundant sequences are more likely to pair with one another.

As noted above, the tanglegrams can be anchored using VH and VL that are known to pair with each another. These sequences may be obtained using any suitable method. For example, VH and VL sequences may be amplified from individual B cells (obtained by plating the collected B cells at a single-cell dilution) by single-cell RT-PCR. Alternatively, the collected B cells can be fused with a suitable fusion partner (as described above) and the VH and VL sequences can be amplified from a hybridoma. The number of sequences used for anchoring a tanglegram may vary depending on the number of sequences being analyzed. In some instances, on average, at least 10%, at least 20%, or at least 30% or at least 50% of the sequences in a tanglegram should be anchored. Depending on the size of the tanglegram, this may be represented by at least 10, at least 20, at least 30, at least 50 or least 100 or more edges. In certain embodiments, one may need to obtain at least 100, at least 500, at least 1,000, at least 5,000, at least 10,000 or more VH and VL sequences that have known pairing.

Figure 10:
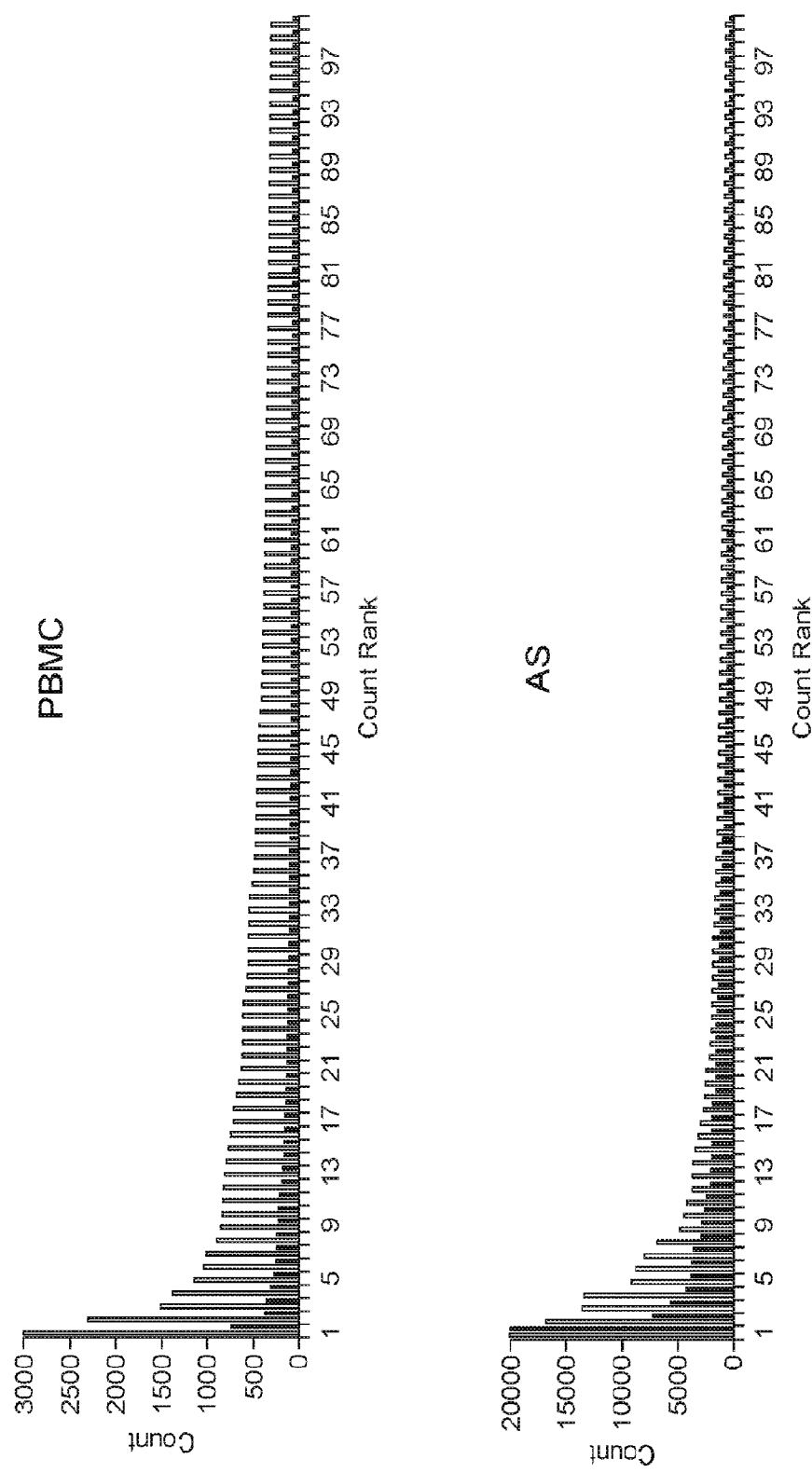
FIG. 10 shows polarization in abundance numbers between AS (enriched and activated) and PBMC samples.

In the sequence data obtained using the present method, there is often a defined number of antibodies, i.e., approximately 10-500 VH and VL sequences, that are much abundant than the rest and that can be readily ranked by their abundance (see FIG. 10). In some embodiments, this "polarization" often allows one to pair the VH and VL sequences by their abundance and produce antibodies that bind to the original antigen. As such, in certain embodiments, after the sequences have been obtained, the VH and VL sequences can be independently ranked in accordance with their abundance (i.e., with the with the most abundant sequence first, the second most abundant sequence next, and the third most abundant sequence next, and so on). This ranking step may be based on the sequence reads alone where, for example, all sequence reads that are identical or very similar (i.e., at least 98% or 99% identical to accommodate sequence errors) are placed into a group and the number of sequence reads for each group is counted. The ranking stem may also be done using translated sequences, where the sequence reads are grouped by at least the CDR3 regions (e.g., only the CDR3 regions, all of the CDRs, or the entire variable region) encoded by the sequence reads. In this example, all sequence reads that encode antibodies with similar or identical CDR3 regions, CDRs or variable regions (i.e., at least 98% or 99% identical or having one or two amino acid substitutions to accommodate sequence errors) are placed into a group and the number of sequence reads for each group is counted.

After the ranking is done, the heavy and light chains may be paired together in accordance with their ranked order of abundance. In this example, the most abundantly ranked heavy chain sequences are paired with a correspondingly ranked light chain sequence, i.e., the first, second, third, fourth and fifth most abundant heavy chain sequence are paired with the first, second, third, fourth and fifth most abundant heavy chain sequence. Antibodies containing such paired heavy and light chains may be made and tested. Rank ordering is described in US20110312505, Haessler (Methods Mol. Biol. 2014 1131:191-203) and Reddy (Nat Biotechnol. 2010 28:965-9).

In certain cases, the rank order of two or more sequences may be ambiguous because they have a similar abundance (e.g., an abundance that is within 10% or 20% of one another). For example, the most abundant heavy chain sequence may be represented by 10,000 sequence reads, whereas the second and third most abundant heavy chain sequences may be represented by 5,500 and 6,000 reads respectively. In this example, the second and third heavy most abundant chain sequences may have an ambiguous ranking and, as such, can be difficult to determine if they are correctly ranked.

Ambiguous rankings can be resolved by analyzing the lineages of the sequences that are ambiguously-ranked and the lineage of the correspondingly ranked sequences from the other chain. This "local" lineage analysis method generally involves constructing two separate lineage trees showing the theoretical relationship of the most abundant heavy and light chain sequences (e.g., 2, 3, 4, 5, 6, 7, 8, 9 or 10 or more of the most abundant sequences) with other, similar, sequences represented in the sequencing data. One lineage tree is constructed using the VH sequences and the other lineage tree is constructed using the VL sequences. In attempting to resolve an ambiguity in the ranking of two light chains, one can look at the phylogenetic tree of the heavy chain (in which the correspondingly ranked sequences are not ambiguous), and determine which order the two light chains should be ranked. For example, if two heavy chain sequences map to a clade that contains a relatively large number of sequence that differ from one another by one or two amino acids (which have resulted from affinity maturation), then the corresponding light chain sequences are likely to map to a clade that contains a relatively large number of sequence that differ from one another by one or two amino acids. In another example, if one heavy chain sequence maps to a clade that contains a relatively large number of sequence that differ from one another by one or two amino acids and the other heavy chain sequences maps to a side branch off that clade, then the corresponding light chain sequences are likely to map to a similar clade and a side branch off that clade. In another example, if two heavy chain sequences map to different branches in a highly branched clade, then the corresponding light chain sequences likely map to different branches in a highly branched clade. In another example, if a heavy chain sequence maps to a basal clade (a clade that is near the root of the tree), then the corresponding light chain sequence likely maps to a basal clade. Therefore, in attempting to resolve potential ambiguities in a ranking of, e.g., a VH sequence, one can look at the phylogenetic tree of the VL sequences (in which the correspondingly ranked sequences are not ambiguous), and determine which ranking is correct, based on where the correspondingly ranked sequences are on that tree.

Figure 5:
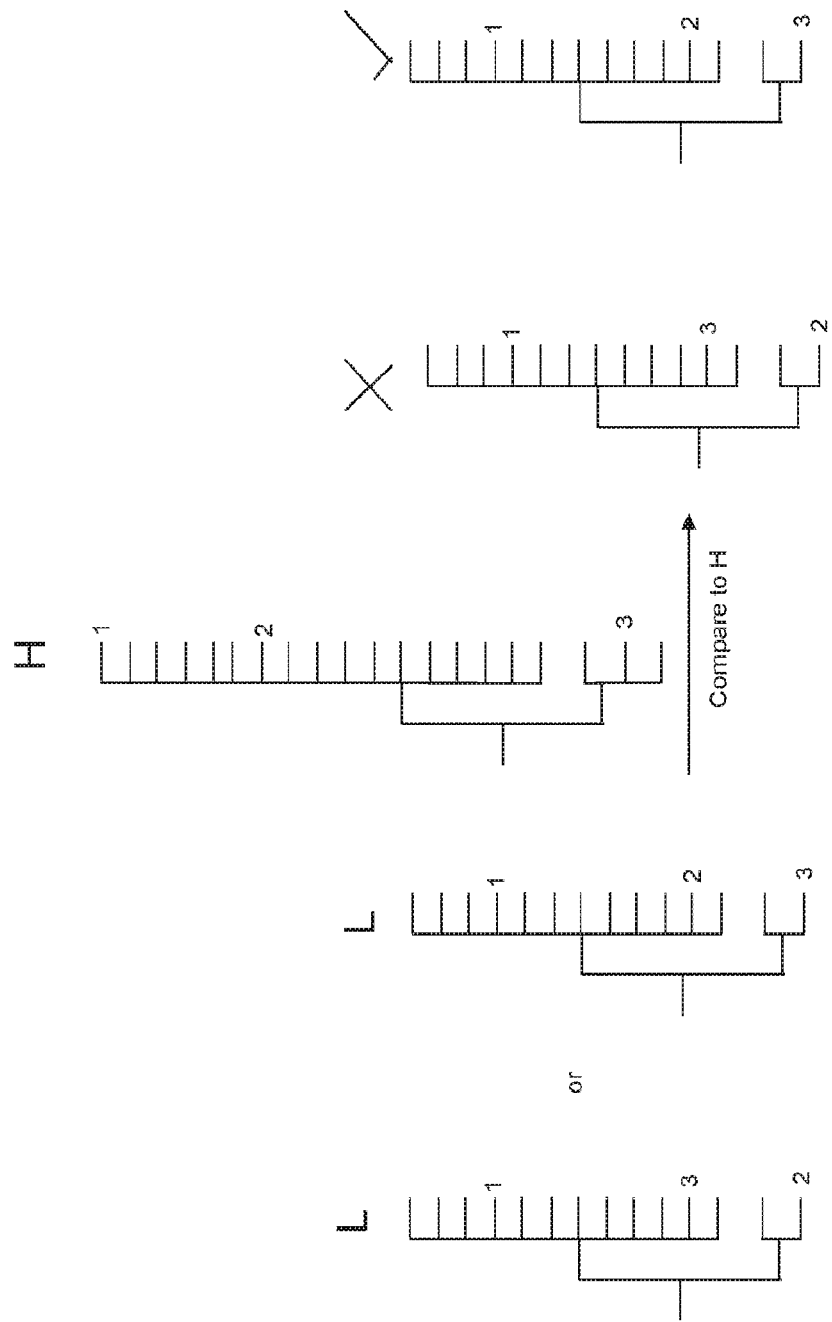
FIG. 5 schematically illustrates a way for resolving an ambiguously ranked light chain sequence.

This concept is illustrated in FIG. 5. In FIG. 5, the second and third most abundant light chain sequences are ranked ambiguously. By comparing the lineage tree for the most abundant light chain sequences to the lineage tree for the most abundant heavy chain sequences, one can resolve the ranking of the light chain sequences and determine which one correctly pairs with which heavy chain. In this example, the second and third most abundant light sequences pair with the second and third most abundant light chain sequences in some combination. Based on the VH and VL trees, one can deduce that overall, the pairing is likely to be correct because the branching pattern of the heavy and light chain trees is similar; b) based on the heavy chain tree, the second most abundant light chain sequence likely is likely to be in the same clade as the most abundant heavy light sequence, and c) based on the heavy chain tree, the third most abundant light chain sequence is likely to be in a side branch of clade that contains the second most abundant light chain sequence. Based on this analysis, the ambiguity of the ranking can be resolved. In this case, the most abundant heavy chain pairs with the most abundant light chain, the second most abundant heavy chain pairs with the second most abundant light chain, and the third most abundant heavy chain pairs with the third abundant light chain. Even if such analysis does not remove all ambiguities, the candidate pairings can be narrowed down and tested.

In certain embodiments, the method may involve (a) obtaining a sample of cells from an animal that has been immunized by an antigen, wherein the sample comprises B cells; (b) enriching for a population of antigen-specific B cells that comprise cell surface antibodies that are specific for the antigen by: i. contacting at least $10^5$ of the cells in the sample, en masse, with the antigen or a portion thereof; and ii. isolating cells that bind to the antigen or portion thereof;

and (c) activating the enriched B cells, en masse, in the presence of the antigen or portion thereof, to produce the enriched population of antigen-specific plasma cells; (d) making cDNA from the enriched population of antigen-specific plasma cells; and (e) obtaining a plurality of heavy chain variable domain sequences and a plurality of light chain variable domain sequences by sequencing the cDNA; and (f) comparing the sequences obtained in (e) to a plurality of heavy chain variable domain sequences and a plurality of light chain variable domain sequences obtained by sequencing a second portion of the sample of (a). This implementation of the method may be used to identify sequences that truly encode antigen-specific antibodies, to identify antibodies that are produced by B cells that have potentially not been activated in the original sample, without the need to perform a screen.

As noted above, the method may be multiplexed in that an animal may be immunized with complex immunogen, and antigen-specific cells for each of a plurality of antigens of the immunogen may be enriched separately from one another. In these methods, two, three, four, five or more, at least 10, at least 20, at least 50, or at least 100 or more different supports may be used to separately isolate the different antigen-specific B cells, thereby allowing a single animal to be immunized with a complex immunogen. B cells that are specific for each antigen of interest can be enriched separately from one another. In some embodiments, the antigen-specific cells can then be activated and collected, as summarized above, to provide a plurality of populations of cells, each specific for a different antigen. These methods generally involve: (a) obtaining a sample of cells from an animal that has been immunized by an complex immunogen, wherein the cells comprise B cells; (b) enriching for a first population of antigen-specific B cells that comprise cell surface antibodies that are specific for a first antigen by: i. binding at least $10^5$ of the cells in said sample, en masse, with the first antigen or a portion thereof; and ii. isolating cells that bind to the first antigen or portion; (c) activating the enriched B cells, en masse, in the presence of the first antigen or portion thereof to obtain a first population of activated B cells; and (d) collecting the first population of activated B cells from the support. This method may comprise (b) enriching for a second population of antigen-specific B cells that comprise cell surface antibodies that are specific for a second antigen of the immunogen by: i. binding at least $10^5$ of the cells in said sample, en masse, with the second antigen or a portion thereof; and ii. isolating cells that bind to the second antigen or portion thereof; (c) activating the enriched B cells, en masse, in the presence of the second antigen or portion thereof to obtain a second population of activated B cells; and (d) collecting the second population of activated B cells activated cells from the support.

Figure 6:
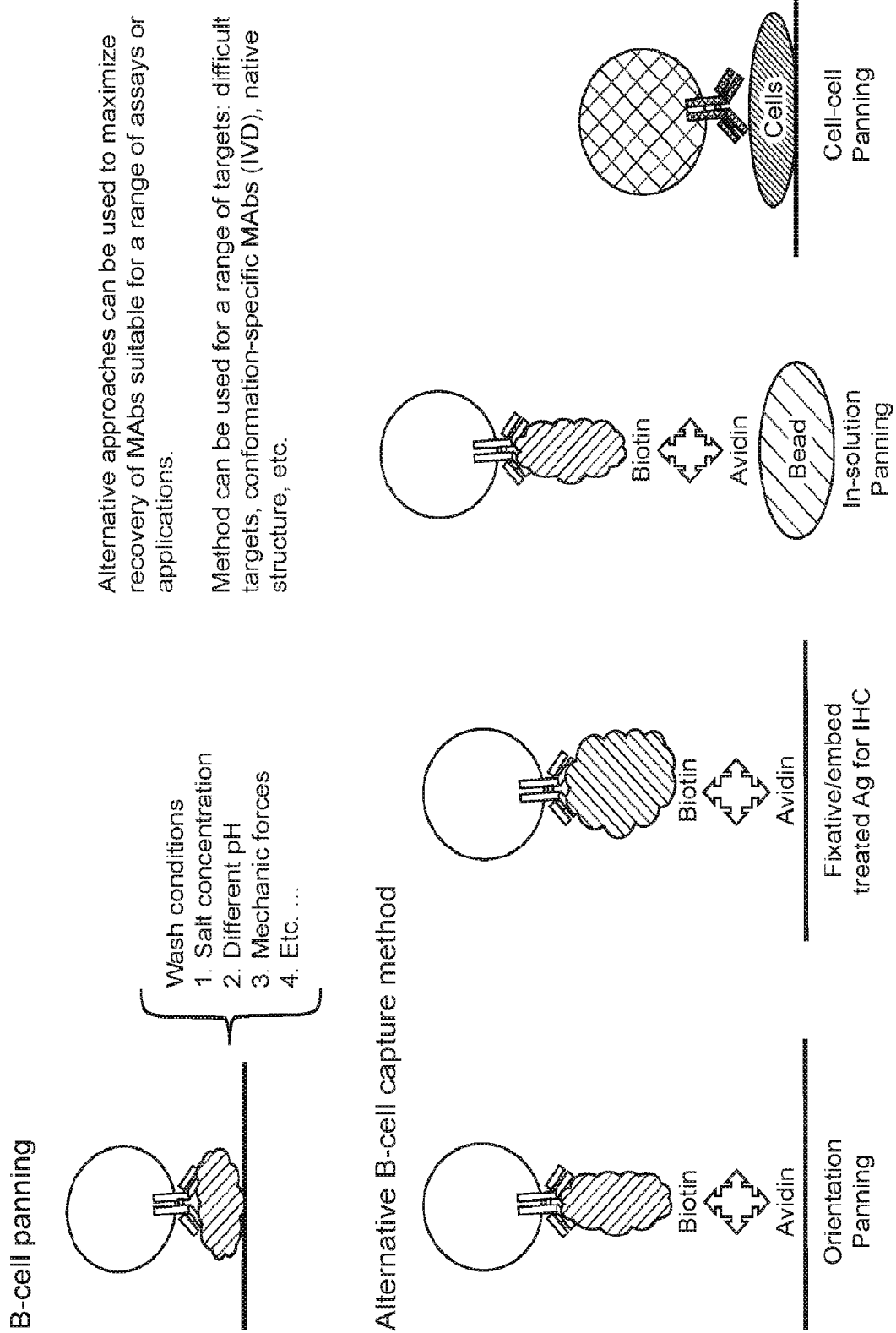
FIG. 6 schematically illustrates how application-specific B cells can be enriched.

Also as noted above, the enrichment step may be tailored to enrich for application-specific antibodies, i.e., antibodies that are selected for a particular use, e.g., FACS, immunohistochemistry, therapeutics, etc.). Examples of this are shown in FIG. 6. In some embodiments, the antigen-specific B cells may be enriched by binding to the antigen under a particular condition, e.g., a particular salt concentration, pH, under a particular mechanical force, temperature, or in the presence of an additive to the binding buffer. In other embodiments, the antigen-specific B cells may be captured using antigens that are presented in a particular orientation (which should make the final antibody more suitable for ELISA assays and the like), fixed/embedded antigen (which should make the final antibody more suitable for IHC assays done on FFPE samples), beads that are linked to the antigen (which should make the final antibody more suitable for immunoprecipitation) and cells (which should make the final antibody more suitable for FACS and cell enrichment applications). These are only examples and others would be apparent.

Once the heavy and light chain sequences are paired, polynucleotides encoding the variable regions of the antibodies are made and expressed. In some cases, the synthesized sequences may be inserted into appropriate vectors for expression, for example, as full length IgGs or single chain antibodies, by transfection of HEK293 cells or another suitable cell type. The nucleic acids, once made, can be operably linked to an expression polynucleotide that will allow for expression, and optionally secretion of a functional antibody from a host cell. In particular cases, the expressed antibody may be a single chain antibody. Strategies for producing a recombinant antibodies, e.g., in mammalian, bacterial and yeast host cells are well known. Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

After a recombinant antibody is produced by another host cells, it may be tested in a variety of assays and, depending on how the antibody is going to be used, it may be humanized. For example, an antibody may be tested in a binding assay (e.g., an ELISA, a FACS assay or using immunohistochemistry) or an activity assay (which may be in vivo, in vitro or in a cell-free system), methods for which are well known (see, e.g., US20040067496).

An antibody produced by the instant methods finds use in, for example, diagnostics, in antibody imaging, and in treating diseases treatable by monoclonal antibody-based therapy. In particular, an antibody humanized by the instant methods may be used for passive immunization or the removal of unwanted cells or antigens, such as by complement mediated lysis or antibody mediated cytotoxicity (ADCC), all without substantial immune reactions (e.g., anaphylactic shock) associated with many prior antibodies.

In one embodiment, a humanized version of an identified antibody is provided. In certain cases, humanized antibodies may be made by substituting amino acids in the framework regions of a parent non-human antibody to produce a modified antibody that is less immunogenic in a human than the parent non-human antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519, 596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject antibody may be humanized according to the methods set forth in published U.S. patent applications 20040086979 and 20050033031. Accordingly, the antibodies described above may be humanized using methods that are known in the art.

In one embodiment of particular interest, a subject antibody may be humanized in accordance with the methods set forth in great detail in U.S. Pat. No. 7,462,697 which application is incorporated by reference in its entirety. In general, this humanization method involves identifying a substitutable position of an antibody by comparing sequences of antibodies that bind to the same antigen, and replacing the amino acid at that position with a different amino acid that is present at the same position of a similar human antibody. In these methods, the amino acid sequence of a parental antibody is compared to (i.e., aligned with) the amino acid sequences of other antibodies that are clonally related to the parental antibody to identify variation tolerant positions. The amino acid sequence of the variable domain of the parental antibody may be compared to a database of human antibody sequences, and a human antibody that has an amino acid sequence that is similar to that of the parental antibody is selected. The amino acid sequences of the parental antibody and the human antibody are compared (e.g., aligned), and amino acids at one or more of the variation tolerant positions of the parental antibody are substituted by correspondingly positioned amino acids in the human antibody. In this humanization method, the CDR regions of the antibody may be humanized in addition to the framework regions.

EXAMPLES

The following examples are provided in order to demonstrate and further illustrate certain embodiments and aspects of the present invention and are not to be construed as limiting the scope thereof.

Overview

One of the challenges in the application of next generation sequencing (NGS) technology to monoclonal antibody development is to identify, among millions of VH/VL sequences, the subset representing targeted antigenic response. Integration of experimental design with bioinformatics (data mining strategies) is essential to achieve this objective. Described herein is a new approach that combines B cell enrichment, activation and NGS to identify antigen-specific IgG with higher confidence and better resolution.

B-cells derived from the peripheral blood of an immunized animal can be used as the starting material. This sample contains a large population of B-cells of different differentiation stage and specificity, immature, naïve and plasma B-cells and it is estimated (based on published flow cytometry analysis) that only 0.1-1% of the circulating B-cells are related to the antigenic response following immunization. To unravel this complexity, narrow the scope to antigen-specific B-cells and increase sensitivity (sequencing depth), B-cells are selected on solid support for affinity to the antigen. In-vitro proliferation promotes cell division and differentiation of antigen-specific B-cells, which are collected and sequenced. The transition of an antibody-presenting B-cell (which should in theory be memory B cells) into an antibody-producing B-cell is accompanied by a strong increase in IgG mRNA expression, which can be detected by NGS and their abundance can be estimated by counting sequence reads. In addition, only the B-cells initially activated by interaction with the antigen differentiate into plasma cells.

Depending on how the method is implemented, the method provides greater sensitivity, a reduction in "noise" and is highly scalable, unlike other methods. Greater sensitivity is achieved by enriching for antigen-specific B-cells: enrichment on antigen coated plates may allow for a 5-10× enrichment in B cells expressing antigen-specific IgG, and selecting for B cells that express rare monoclonal antibodies that would otherwise be missed without enrichment. A reduction is noise can be achieved by activating the antigen-specific B-cells. In this step, only the B-cells that are bound to the antigen proliferate and differentiate into plasma cells. The significant increase in mRNA expression from the activated population of cells helps distinguish those sequences from noise that is inherent in more traditional selection methods (e.g., sequences from plasma cells that non-specifically bind during enrichment). Finally, the method is highly scalable in that a large population of cells (e.g., of 5-10 million cells) can be subjected to enrichment and used in the method.

Example 1

Protocol for PBMC Isolation, Enrichment and Activation

1) Antigen Coating and Blocking:
   1. Sterile filter the antigen solution by using a 0.22 μm syringe filter.
   2. Coat a high affinity dish with antigen (1.5 ug/ml) in 10 mL of PBS.
   3. Incubate overnight at 4° C.
   4. Aspirate the plate the next morning and wash 2× with 10 ml PBS.
   5. Block the plate by adding 10 ml 5% FBS/PBS solution. Incubate for 2 hours at room temperature or 30 minutes at 37° C.
   6. Aspirate the plate and then wash 1× with 10 ml 1640 RPMI media
2) PBMC Isolation:
   1. Add 15 ml of gradient media (Ficoll-Paque Premium 1.084) into a Leucosep lymphocyte separation tube. It should be above the white membrane. Heavily shake the Ficoll bottle before use.
   2. Centrifuge at 1200 rpm for 30 seconds. The gradient should be below the white membrane.
   3. Dilute the rabbit blood 1:1 with room temperature PBS. Then pour 20 mL of the diluted rabbit blood into the Leucosep tube. It should layer on top of the membrane and gradient media.
   4. Centrifuge at 1500 rpm for 30 min.
   5. Using a Pasteur pipette, carefully transfer the PBMC layer into a new 50 ml tube (be careful to avoid mixing the PBMC layer with the serum layer).
   6. Wash with 45 ml of DPBS and centrifuge at 1150 rpm for 10 min to collect the cells. Do not aspirate the supernatant as you may aspirate cells, instead pour it off into a waste container.
   7. Repeat step 6.
   8. Resuspend the cell pellet in 5 ml B-cell fusion media and count the number of viable cells by hemocytometer or FACS.

3) Panning:
  1. Add 5M PBMCs to a high affinity dish (coated, blocked, and washed) with 5 ml B-cell fusion media (cell density 1 M/ml). If cell number lower than 5M, put all the cells into 5 ml.
  2. Incubate at 37° C. for 90 min with slow agitation (50 rpm).
  3. Aspirate the media and wash 2× with of 5 ml B-cell fusion media. Add the media slow, and always to the same spot on the dish. Check the dish with a microscope after each wash. If the number of attached cells is low, reduce the number of wash steps; if cell number is high and there are many cells are in suspension then wash one more time. Two washes are standard.
4) B-Cell Culture:
  1. After washing, add 10 ml of B-cell fusion media in the dish.
  2. Then add 10 ml CD40L feeder cell media in the dish.
  3. Incubate at 37° C. and 5% $CO_2$.
  4. After 5-6 days use a microscope to check the cell status and number, if media is yellow and many cells can be seen under the microscope, then add 10 ml of B-cell fusion media to the dish and do the fusion on the $7^{th}$ day; if cells grow up and expand and media is still pink, do the fusion on the $7^{th}$ day; if cell number is low, add 10 ml Feeder cell media (without feeder cell) and do the fusion on the $10^{th}$ day.

Example 2

Protocol for Hybridoma Production

5) B-Cell Fusion
  1. Harvest the B-cells into a 50 ml tube.
  2. Count the number of live cells with trypan blue or FACS.
  3. Transfer 8 M B-cells to another new 50 ml tube and add 4 M 240E-W2 into the tube (if the cell number is less than 8M, then add 240E cell number at a ratio of 2:1).
  4. Centrifuge at 1500 rpm for 5 min.
  5. Aspirate the supernatant completely while being careful to not lose any cells.
  6. Add 0.3-0.4 ml of pre-heated PEG, slowly (should take 10-30 s) to the bottom of the tube using a sterile Pasteur pipette (should take 1 min total).
  7. Slowly add 21 mL of pre-heated 1640 RPMI media (should take 1 min).
  8. Slowly add 21 mL of pre-heated B-cell growth media (should take 1 min).
  9. Closed tube cap, invert the tube slowly to mix the medias.
  10. Add feeder cells (240E-W2) into the tube ($2 \times 10^6$ of 240E per 1×96 plate).
  11. Spin down the cells at 1100 rpm for 5 min.
  12. Aspirate the supernatant.
  13. Add 1 ml of 240E growth media and resuspend the cell pellet with a transfer pipette.
  14. Dilute the cells with B-cell growth media and add into 4 96-well plates (100 ul/well).
  15. After 24 hours, add 2× HAT 240E-W2 media to the plates (100 ul/well).

Example 3

Preparation of VH and VL Libraries

B-cells from peripheral blood were enriched and activated according to the protocol described above. 5 million cells were collected 5-8 days after proliferation, the cells were then lysed in TRIzol reagent (Life Technology) and total RNA was isolated using RNeasy purification kit according to the manufacturer's protocol (Qiagen). RNA concentration was measured with an ND-1000 spectrophotometer (Nanodrop). A total of 2 ug of total RNA was combined with TCL buffer at a 1:8 v/v ratio, aliquot in 2 wells (one for each VH and VL library), and mRNA was then isolated by hybridization to well-immobilized oligo-dT according to manufacturer's protocol (TurboCapture, Qiagen).

First-strand cDNA synthesis was carried using the ImProm II reverse transcription system (Promega) by adding reagents directly to the wells containing the immobilized mRNA. After reverse transcription, the wells are washed 3 times with 100 ul 10 mM Tris-Cl buffer (pH 7.5). VH and VL genes are amplify by PCR using a mix of slightly degenerated IgG-specific primers (see below). The 80 ul PCR reaction consisted of 0.2 uM of forward and reverse primer mixes, 1× precision buffer (Agilent), 0.2 mM dNTP and 5U TaqPlus precision (Agilent). The thermocycler program was: 95° C. for 3 min and 34 cycles (95° C. for 40 s, 62° C. for 30 s, and 72° C. for 50 s); 72° C. for 10 min; 4° C. storage.

PCR products were gel purified (Qiagen Gel extraction Kit) and yield quantified using an ND-1000 spectrophotometer (Nanodrop). Illumina adapters and compatible indices are then added by limited cycle PCR. The 30 ul PCR reaction consisted of 20 ng PCR product (see above), 5 ul of each Nextera XT index primer (N7xx and N5xx) and 2× KAPA HiFi HotStart Ready Mix. The thermocycler program was: 95° C. for 3 min and 8 cycles (98° C. for 20 s, 62° C. for 15 s, and 72° C. for 50 s); 72° C. for 10 min; 4° C. storage. PCR products were gel purified (Qiagen Gel extraction Kit) and submitted for Illumina MiSeq 2×300 sequencing (UC Davis Genome Center).

VH Amplification Primers
Forward:
(SEQ ID NO: 1)
5'-TCGTCGGCAGCGTCAGATGTGTATAAGAGACAGATGGAGACTGGGCT
GCGCTGGCTTCTCC-3'

Reverse (1:1 ratio)
(SEQ ID NO: 2)
5'GTCTCGTGGGCTCGGAGATGTGTATAAGAGACAGCAGTGGGAAGACTG
ACGGAGCCTTAG-3'

(SEQ ID NO: 3)
5'GTCTCGTGGGCTCGGAGATGTGTATAAGAGACAGCAGTGGGAAGACTG
ATGGAGCCTTAG-3'

VK Amplification Primers
Forward:
(SEQ ID NO: 4)
5'-TCGTCGGCAGCGTCAGATGTGTATAAGAGACAGATGGACACGAGGGC
CCCCAC-3'

Reverse (9:0.5:0.5 ratio)
(SEQ ID NO: 5)
5'GTCTCGTGGGCTCGGAGATGTGTATAAGAGACAGTGGTGGGAAGAKGA
GGACAGTAGG-3'

(SEQ ID NO: 6)
5'GTCTCGTGGGCTCGGAGATGTGTATAAGAGACAGTGGTGGGAAGAKGA
GGACACTAGG-3'

(SEQ ID NO: 7)
5'GTCTCGTGGGCTCGGAGATGTGTATAAGAGACAGTGGTGGGAAGAKGA
GGACAGAAGG-3'

Example 4

Data Analysis Methods

Pre-Processing:

Demultiplexing of the pooled libraries (n=10-15 per sequencing run) and FastQ file generation was performed using MiSeq Reporter software pre-installed with the Illumina MiSeq instrument. FastQ files contains sequencing and associated Phred quality score for each base pair. We used NGS QC Toolkit, an open source software, to evaluate the overall performance and quality of the NGS sequencing run (PLoS One. 2012; 7(2):e30619). The paired-end reads contained in the Illumina R1 (forward) and R2 (reverse) files are combined using PEAR (Bioinformatics. 2014 Mar. 1; 30(5): 614-20) to reconstitute the VH or VK region of the antibody repertoire. The following parameters were used for sequence assembly: Each sequence are trimmed at the occurrence of two consecutive base pair of a Phred quality score less than 20; the minimal overlap length equal 50 base pair or greater; the p-value of the alignment is greater than 0.0001; and the length of the assemble sequence greater than 300 base pair. The FASTQ file was converted to FASTA format using FASTX-toolkit, a collection of command line tools for Short-Reads FASTA/FASTQ files preprocessing (hannonlab.cshl.edu/fastx_toolkit/) and the sequences are translated in amino acid for further analysis. Sequences with a "STOP" codon within the ORF are filtered out the dataset. A curated dataset is created by parsing the sequences for identical amino acid sequences and filtering out sequence redundancy. The number of identical sequence is recorded in a log file to capture the frequency of reads for a particular VH/VL sequences, i.e. reads count.

Mapping of VH/VL Structural Domains:

The Kabat numbering scheme is a widely adopted standard for numbering the amino acid residues within the variable light and heavy chain (Al-Lazikani et al., (1997) JMB 273, 927-948; summary: http://www.bioinf.org.uk/abs/). The Chothia numbering schema is identical to Kabat, but places the insertion in CDR-L1 and H1 at the structurally correct positions (Al-Lazikani et al., (1997) JMB 273, 927-948). This is the numbering schema that we used for mapping structural domains within the variable IgG region, i.e. delimitating the leader, FRM1, CDR1, FRM2, CDR2, FRM3, CDR3 and FRM4 domains. The VH/VL Framework 1-3 are generally highly conserved amino acid sequences, while the CDR1-3 are highly variable. A database was created based on approximately 2300 know MAbs VH and VL sequences, which capture sequence variations within the conserved Leader+FRM1, FRM2, FRM3 and FRM4. The databases are then used as BLAST database to precisely delineate the Leader+FRM1, FRM2 and FRM3 of each sequences within the antibody repertoire NGS. Intervening amino acid sequences are assigned to the variable CDR1, CDR2 and CDR3 domain, respectively.

Phylogenetic Pairing of Heavy and Light Chains:

A descending ordered list of VH or VL sequences is build based on the reads count determined at the pre-processing step. Frequency is a particular IgG sequence is determined by a) the number of clonal B-cells present in the sample and, b) the average expression level of this specific sub-population. Therefore, a direct correlation can be seen between VH and VL sequence counts. The top most predominant sequences are selected, in equal number in each ordered list, to construct an amino acid multiple alignment of the entire VH or VL region using CLUSTALX2 (http://www.clustal.org/). The parameters for the multiple alignment are: open gap penalty=25; gap extension=0.2; delay divergent sequences=30%; and protein weight matrix=identity matrix. The output unrooted trees was visualized using Dendroscope 3 (http://ab.inf.uni-tuebingen.de/software/dendroscope/). Phylogenetic trees derived from VH and VK sequences are compared to each other's using the tanglegram algorithm available in Dendroscope.

Example 5

Protocol for B-Cell Staining for Analysis by Flow Cytometry

Peripheral blood mononuclear cells (PBMCs) were isolated from a rabbit that was immunized with keyhole limpet hemocyanin (KLH, Pierce Biotechnology) and boosted two weeks prior to cell isolation with 0.5 mg KLH in phosphate buffered saline (PBS). Approximately five million of the purified PBMCs were incubated in media on a KLH coated petri dish (coated overnight with 1.5 ug/mL KLH in PBS, blocked with 10% fetal bovine serum (FBS), and washed two times with PBS) for 1.5 hours at 37° C. The cell coated petri dish was then washed three times with media and all non-adhering cells were collected and transferred to a new polystyrene petri dish. The panned cells and the non-adhering cells were cultured in separate dishes for six days using the previously described B-cell culture conditions. The resulting cell populations were then harvested and stained for flow cytometry analysis.

For staining, approximately four million cells were collected from the panned and the non-adhering cell cultures and resuspended for staining in 400 uL 10% FBS in PBS. The cells were first surface stained for 20 minutes at 4° C. with goat anti-rabbit IgG Fc specific Alexa Fluor 647 conjugate (Jackson Immunoresearch, 1:100 dilution) and biotinylated KLH (prepared using Pierce Biotechnology EZ-Link Sulfo-NHS Biotinylation Kit, 1 ug/100 uL). Following primary surface staining, the cells were washed one time with 10% FBS in PBS and then incubated with streptavidin Dylight 405 (Pierce Biotechnology, 1:200 dilution) for 10 minutes at 4° C. Next, the cells were washed two times with 10% FBS in PBS, fixed using 2% paraformaldehyde in PBS at room temperature for 20 minutes, and then washed one time with PBS. For intracellular staining, the samples were permeabilized using 0.25% saponin/10% FBS in PBS for 5 minutes, pelleted, and then stained with goat anti-rabbit IgG Fc specific Alexa Fluor 488 conjugate (Jackson Immunoresearch, 1:100 dilution) and KLH-perCP (Abcam perCP conjugation kit, 1 ug/100 uL) at room temperature for 25 minutes in 400 uL of 0.25% saponin/10% FBS in PBS. Finally, the cells were washed two times with 0.25% saponin/10% FBS in PBS and stored in 1% paraformaldehyde in PBS until analysis.

Results

Sequence Analysis

Figure 7A:
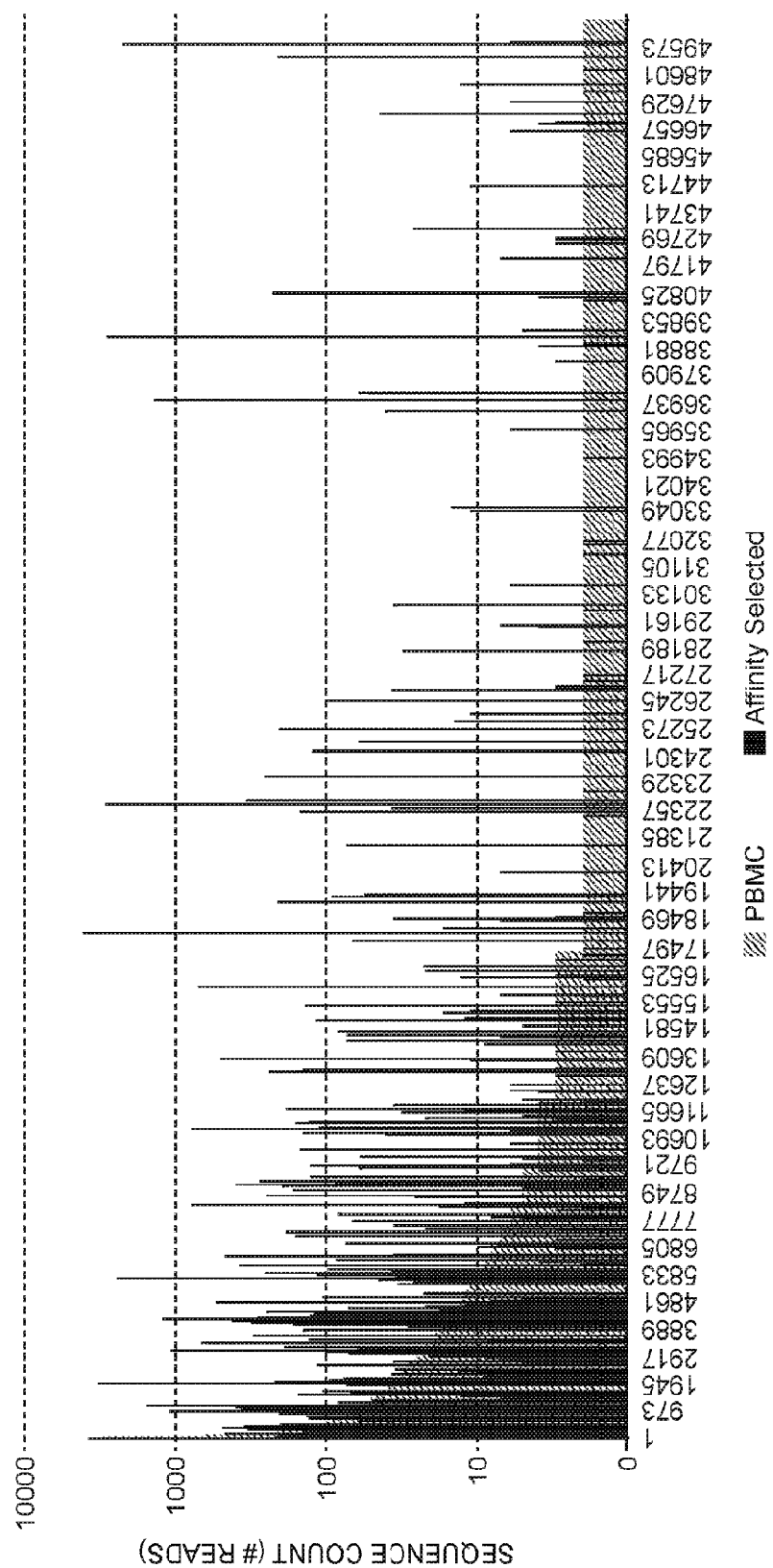
FIGS. 7A and 7B show a comparative analysis of VH sequences recovered from the NGS of total PBMC versus B-cells after antigen specific panning and proliferation (BPP).
Figure 7B:
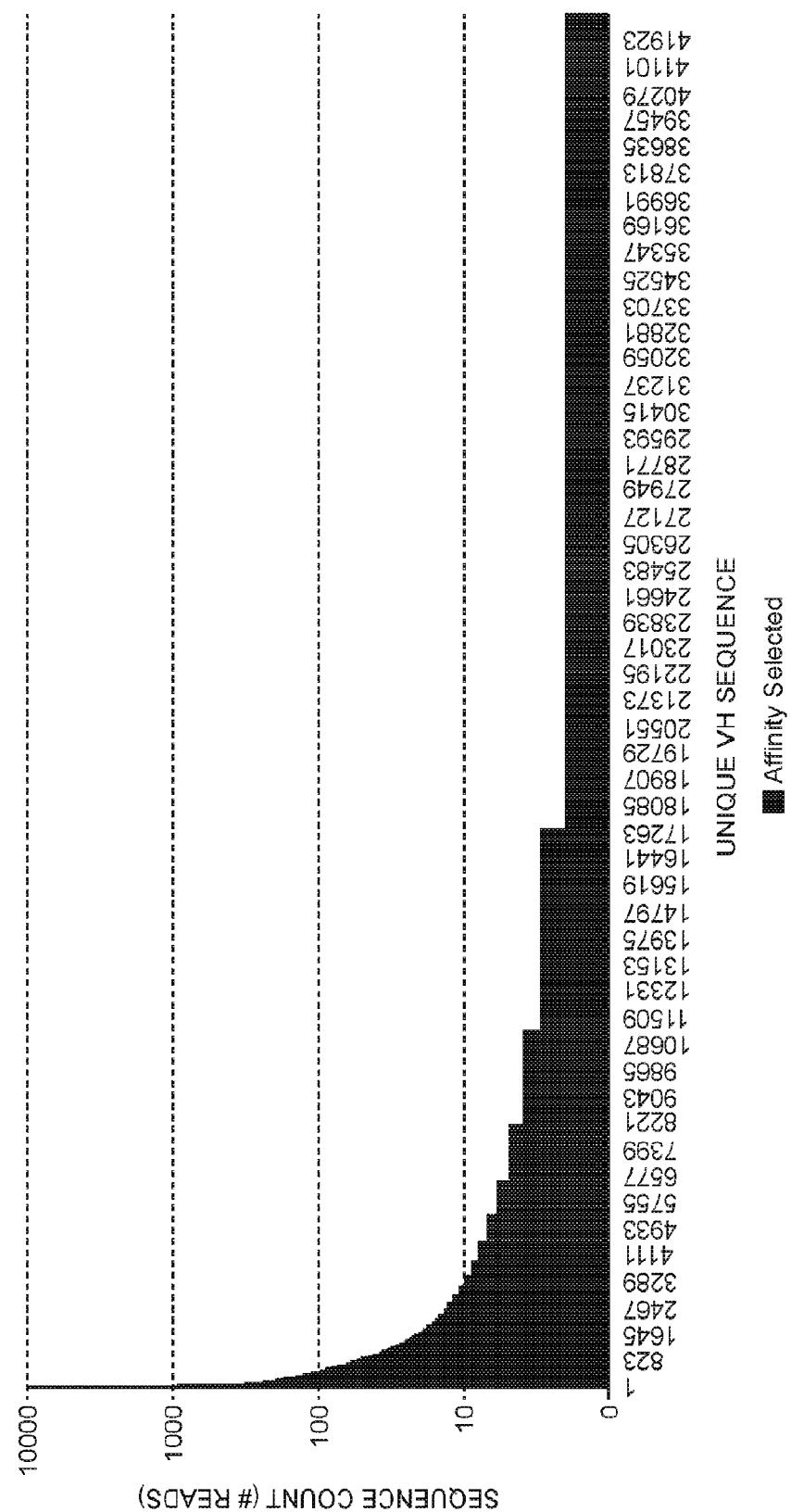

FIGS. 7A and 7B show a comparative analysis of VH sequences recovered from the NGS of total PBMC versus B-cells after antigen specific panning and proliferation (BPP). Each column in FIGS. 7A and 7B represents a unique VH sequence with the abundance displayed on the Y-axis. Overlapping columns in FIG. 7A represent identical sequences recovered from both datasets. FIG. 7B shows sequences recovered solely within the affinity selected sample showing a significant increase in sequencing depth for antigen-specific IgG.

Peripheral blood mononuclear cells were prepared from rabbit immunized with KDR protein as antigen. Two IgG libraries were prepared from independent bleeds. The first library was constructed from total B-cells population (PBMC). The sample contains B-cells associated with the antigenic response as well as naïve B-cells in circulation 10 days after the last subcutaneous antigen injection (last antigenic boost). Unique VH sequences are identified based of the full-length variable IgG domain and frequency for each reads above a threshold of 2 plotted in FIG. 7A (PBMC-RED). 50,513 unique VH sequences were identified by MiSeq 2×300 sequencing.

The second VH library was constructed from affinity selected B-cells to the KDR antigen (Affinity Selected—Blue). B-cells captured on solid support are then proliferated in-vitro in presence of CD40L, KDR antigen and cytokines, which promotes antigen-dependent memory B-cell differentiation. In addition, only the B-cells initially activated by interaction with the antigen differentiates into more mature b-cells. The transition of an antibody-presenting B-cells (memory B cells) into an antibody-producing B-cells is accompany with a strong increase in IgG mRNA expression, which can be detected by NGS (read counts).

Unique VH sequences are identified from the dataset in association with their frequency (number of sequence reads) within the NGS dataset. The data is plotted in FIGS. 7A and 7B. The subset of Affinity-selected sequences present in total PBMC is plotted alongside the corresponding PBMC sequences, illustrating that only a small fraction of antigen-specific B-cells is present in total PBMC. 542 unique VH sequences are in common between PBMC and Affinity-selected/proliferated B-cells (Affinity Selected—Blue). Approximately 1% of the unique VH sequences found in total PBMC correspond to the antigen-specific B-cells. As expected, mRNA abundance (number sequences reads) is significantly larger in the affinity-selected VH than the corresponding frequency in total PBMC.

As outlined above, affinity selection is providing a significant enrichment in antigen-specific B-cells. This results in an increase in sequencing depth for KDR-specific B-cells and far greater representation within the dataset. FIG. 7B plotted unique VH sequences and their abundance (sequence reads) recovered uniquely from the affinity selected/proliferated dataset. 41,923 additional unique VH sequences were recovered.

Figure 9:
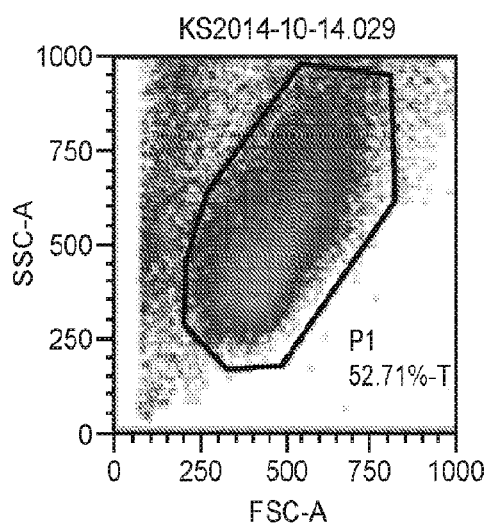
FIG. 9 shows a characterization of a cell culture by flow cytometry.
Figure 9:
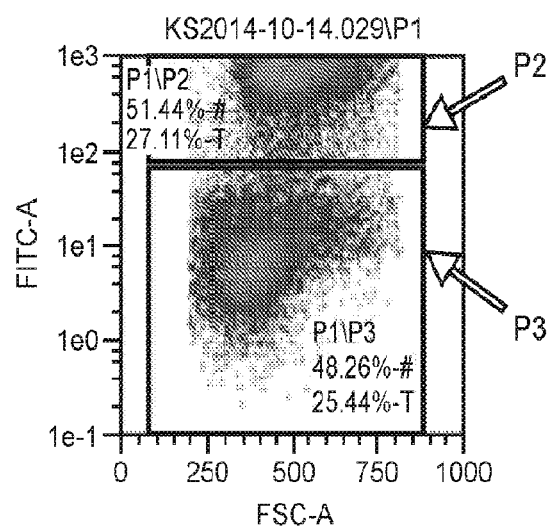
Figure 9:
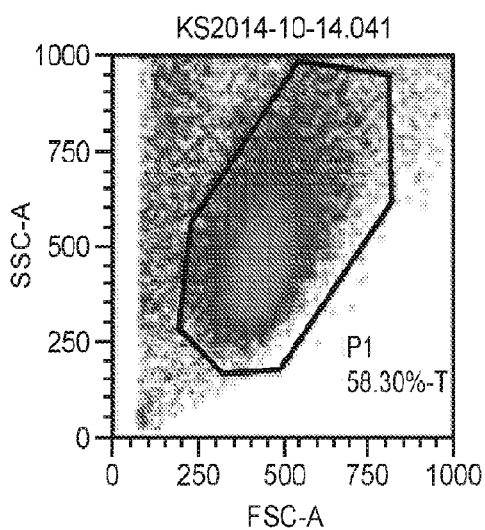
Figure 9:
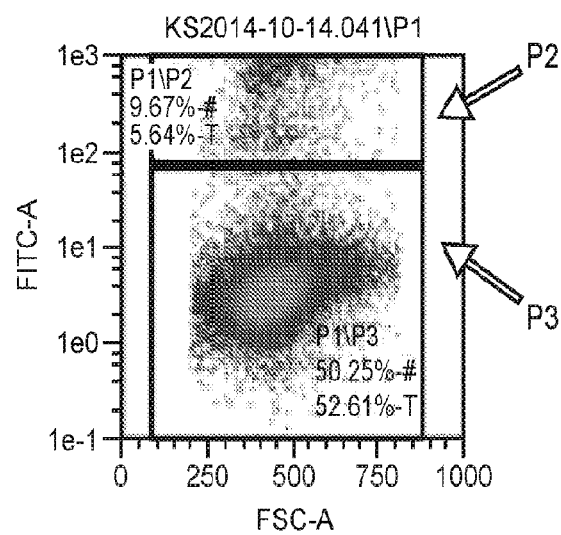
Figure 9:
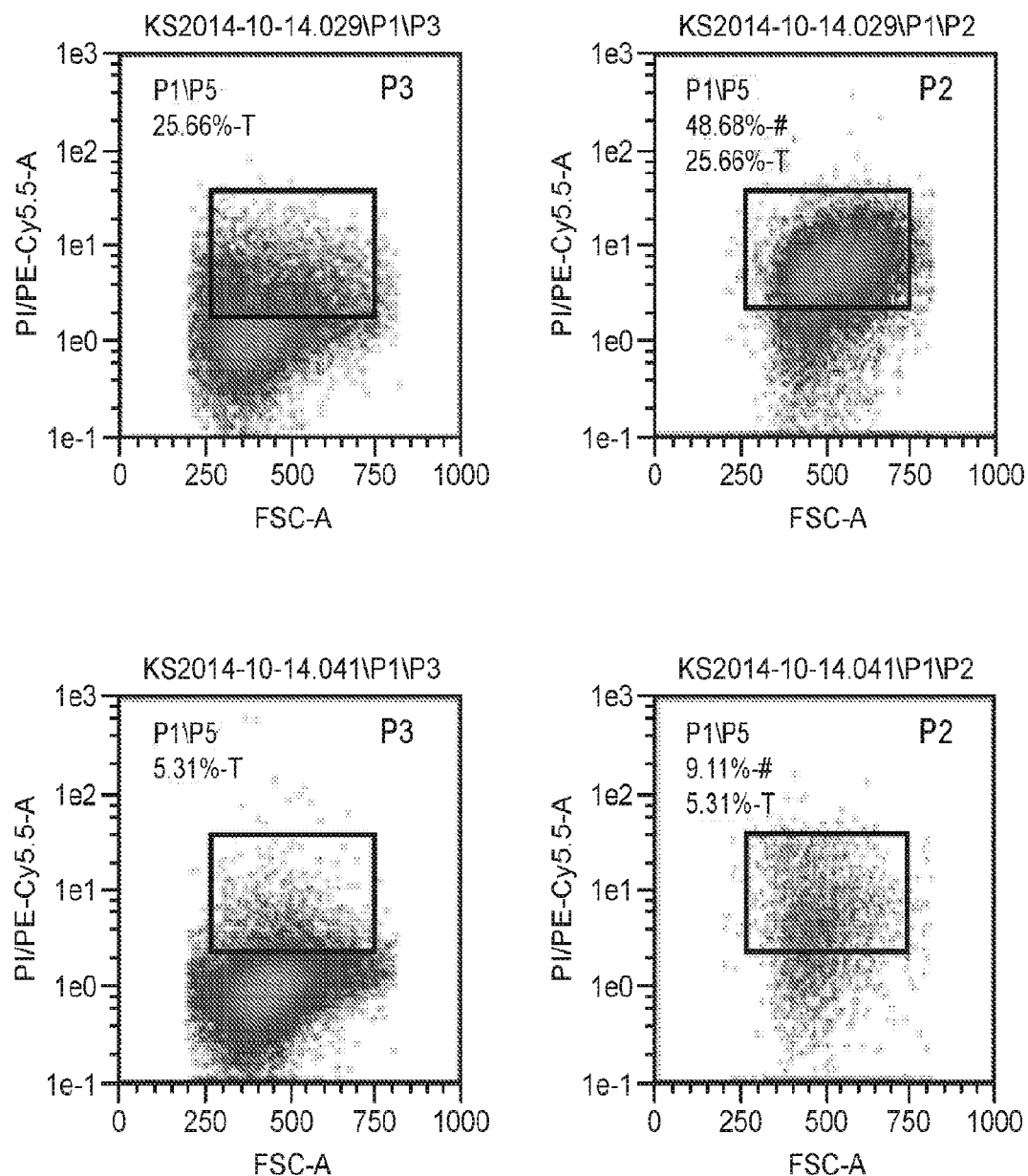

FIG. 9 shows that the sequences obtained from the enriched/activated dataset are highly polarized.

In next generation sequencing implementations of the method, no antibody screening is necessary. Using next generation sequencing one can sample the full antigenic-response, which is represented by 1-5% of the total B-cells in the PBMCs. This data shows that one can identify antigen-specific sequence using NGS data without any screening and with high confidence. For example, the graph shown in FIG. 7A, plots VH sequences before (red) and after BPP (blue). The X-axis lists of all the non-redundant VH sequences above a count of 2 within the datasets. The Y-axis represent the abundance of each sequence. The overlap is represented by sequences that present in both datasets. The next generation sequencing approach can be used to capture the whole repertoire of antigen-specific B cell with high resolution. This allows one to apply rational approaches to the selection of candidate antibodies rather than simply relying on the "luck of the draw" provided by traditional methods. Moreover, abundance is a poor metric when used as sole criteria to identify antigen-specific B-cells because, as shown in FIG. 7A, the most highly abundant sequences are, in fact, false positives.

By overlapping both sequence datasets (before enrichment and activation=PBMC, after enrichment and activation), one can now identify with high confidence which sequences are likely antigen-specific from the noise by looking at differential expression between the two datasets (blue line at least 2× above the red). This approach provides good discrimination from noise.

Furthermore, when sequences recovered from B-cell cloning were compared to the present data, one can see B-cell cloning results only results in the most abundant antibodies. With the present method, we can capture the entire spectrum of sequences, from high to low abundance.

Phylogenetic Pairing of Heavy and Light Chains

Lineage analysis was used to provide structure to the amino acid sequences derived for either VH or VL libraries sequence using the Illumina MiSeq 2×300. During affinity maturation, VH and VL chains co-evolved through somatic hypermutation and gene conversion. The relationship between related sequences can be capture by lineage analysis of multiple alignments. A sorted list was created based on relative abundance (read count) of each sequences within each VH and VL dataset. Read count relate on the clonal expansion (cell division) during the proliferation and expression level of mRNA encoding the VH and VL IgG. Any number a sequences can be used for the analysis. For illustration purpose, we choose the first 100 most abundant unique VH and VL sequences from the ordered list. After multiple alignment using CLUSTALX2, the phylogenetic tree is visualized in Dendroscope.

Defining co-linearity between the VH and VK lineage tree can be challenging due to the diversity in sequences within the CDR1-3. Several tools can be used to approximate VH/VL pairing. Abundance of individual VH and VL sequences was reported to help approximate pairing, but was limited to the most abundant sequences within a highly polarized mouse dataset. Local phylogenetic structures (relationship within related VH and VL sequences at multiple region of the tree) is another criteria that can help aligning the whole trees but often only few are uniquely shared across the phylogenetic trees.

Tanglegram Analysis

FIG. 8 shows a tanglegram of VH and VL sequences obtained using the method described above. A total of 15 VH and VL sequences were linked together using sequences that have a known pairing. As can be seen, the links between the trees are approximately parallel and there are no cross-overs. The approach shown in FIG. 8 relies on the mapping of known VH/VL pairs derived from, e.g., antibodies that have been obtained in a way that the VH and VL pairing is known to each VH and VL phylogenetic tree as multiple anchors for co-alignment. This approach can be used in conjunction to abundance and local phylogenetic structure to increase our confidence in the pairing of large dataset. With this method, a tanglegram algorithm that programmatically resolved the best co-alignment based on the "seed" sequences of known pairing was used. Additional pairs across the phylogenetic trees can then be selected for validation.

Characterization by Flow Cytometry

The cell population obtained from subjecting PBMCs of KLH-immunized rabbits to the BPP procedure was characterized by flow cytometry. Five million PBMC cells were used for B-cell panning and proliferation and the flow through retained and cultured for comparison. Unlike in other model system, such as mouse or human, no surface marker antibodies are available to characterized B-cell population. However, crude approximation can be made by staining with for either the IgG-fc or antigen-specific B-cells.

Four million cells were collected from each culture and stained for intracellular IgG expression, characteristic for antibody producing B-cells, using anti-rabbit IgG-Fc-dylight 488 (FITC on graph). Similarly, the B-cell population producing KLH-specific antibody are detected using KLH antigen conjugated with perCP (PI/PE-Cy5.5 on graph). FIG. 9 panel (A) shows that approximately 50% of the cells recovered after 7 days culture are expressing IgG (P2 sector, high FITC). Less than 10% of the cells in the flow-through stained for IgG, showing that the condition used for panning (37° C., no agitation followed by several washes) capture the large majority of the antigen-specific memory B-cells. Gating of P2 (IgG+) and P3 (IgG−) population revealed that the large majority of the IgG+ B-cell are expressing antibodies interacting with the KLH antigen (FIG. 9 panel (b)).

What is claimed is:

1. A method for producing an enriched population of antigen-specific plasma cells, comprising:
   (a) obtaining a sample of cells from an animal that has been immunized by an antigen, wherein the sample comprises B cells;
   (b) enriching for a population of antigen-specific B cells that comprise cell surface antibodies that are specific for the antigen by:
      i. contacting at least $10^5$ of the cells in said sample, en masse, with the antigen or a portion thereof; and
      ii. isolating cells that bind to the antigen or portion thereof; and
   (c) activating the enriched B cells, en masse, in the presence of the antigen or portion thereof, to produce the enriched population of antigen-specific plasma cells,
   wherein the activating step (c) comprises depositing at least 5,000 enriched B cells into a vessel and culturing the enriched B cells in the vessel to produce a mixed population of antigen-specific plasma cells that comprises at least 100 different clonal populations of antigen-specific plasma cells.

2. The method of claim 1, wherein the cells in the sample are obtained from the spleen, a lymph node, bone marrow or peripheral blood of the animal.

3. The method of claim 1, wherein the enrichment step (b) comprises:
   i. contacting at least $10^5$ of the cells in said sample, en masse, with a support comprising the antigen, or a portion thereof, under conditions by which said antigen-specific B cells bind to the antigen or portion thereof; and
   ii. washing the support to remove unbound cells.

4. The method of claim 1, wherein the enrichment step (b) is done by i. contacting at least $10^5$ of the cells in said sample, en masse, with the antigen, or a portion thereof under conditions by which said antigen-specific B cells bind to the detectably labeled antigen or portion thereof; and
   ii. sorting cells that bind to the antigen or portion thereof.

5. The method of claim 1, further comprising:
   (d) fusing the enriched population of antigen-specific plasma cells with a fusion partner to produce a plurality of hybridomas.

6. The method of claim 5, further comprising
   (e) screening the hybridomas to identify a hybridoma that produces an antibody that binds to the antigen or portion thereof.

7. The method of claim 1, further comprising
   (d) making cDNA from the enriched population of antigen-specific plasma cells; and
   (e) sequencing the cDNA to obtain a plurality of heavy chain variable domain sequences and a plurality of light chain variable domain sequences.

8. The method of claim 7, further comprising:
   (f) selecting a heavy chain sequence and a light chain sequence, and
   (g) testing an antibody comprising the selected heavy and light chain sequences to determine if the antibody binds to the antigen or portion thereof.

9. The method of claim 8, wherein the heavy and light chain sequences are selected by:
   i. obtaining a tanglegram of a plurality of the most abundant heavy and light chain sequences, wherein the tanglegram is anchored using heavy and light chains that are naturally paired with one another;
   ii. selecting a heavy chain sequence and a light chain sequence, wherein the selected heavy and light chain sequences are aligned with one another in the tanglegram; and
   iii. testing an antibody comprising the selected heavy and light chain sequences to determine if the antibody binds to the antigen or portion thereof.

10. The method of claim 1, wherein the animal is a rabbit, a mouse or a chicken.

11. The method of claim 1, wherein the activating is done by CD40 activation.

12. The method of claim 1, wherein the method further comprises collecting the enriched population of antigen-specific plasma cells, wherein the collecting is done by collecting the medium from the support after the isolated B cells are activated.

13. The method of claim 1, wherein the enriching step enriches for antigen-specific B cells that comprise application-specific cell surface antibodies.

14. The method of claim 1, wherein the method comprises:

(a) obtaining a sample of cells from an animal that has been immunized by a complex immunogen, wherein the cells comprise B cells;
(b) enriching for a first population of antigen-specific B cells that comprise cell surface antibodies that are specific for a first antigen by:
i. binding at least $10^5$ of the cells in said sample, en masse, with the first antigen or a portion thereof; and
ii. isolating cells that bind to the first antigen or portion; and
(c) activating the enriched B cells, en masse, in the presence of the first antigen or portion thereof to obtain a first population of antigen-specific plasma cells,
wherein the activating step (c) comprises depositing at least 5,000 enriched B cells into the vessel and culturing the enriched B cells in the vessel to produce a mixed population of antigen-specific plasma cells that comprises at least 100 different clonal populations of antigen-specific plasma cells.

15. The method of claim 14, wherein the method comprises:
(b) enriching for a second population of antigen-specific B cells that comprise cell surface antibodies that are specific for a second antigen of the immunogen by:
i. binding at least $10^5$ of the cells in said sample, en masse, with the second antigen or a portion thereof; and
ii. isolating cells that bind to the second antigen or portion thereof; and
(c) activating the enriched B cells, en masse, in the presence of the second antigen or portion thereof to obtain a second population of antigen-specific plasma cells,
wherein the activating step (c) comprises depositing at least 5,000 enriched B cells into the vessel and culturing the enriched B cells in the vessel to produce a mixed population of antigen-specific plasma cells that comprises at least 100 different clonal populations of antigen-specific plasma cells.

\* \* \* \* \*

```
                            SEQUENCE LISTING

<160> NUMBER OF SEQ ID NOS: 7

<210> SEQ ID NO 1
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 1
tcgtcggcag cgtcagatgt gtataagaga cagatggaga ctgggctgcg ctggcttctc     60
c                                                                     61

<210> SEQ ID NO 2
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 2
gtctcgtggg ctcggagatg tgtataagag acagcagtgg gaagactgac ggagccttag     60

<210> SEQ ID NO 3
<211> LENGTH: 59
<212> TYPE: DNA
<213> ORGANISM: Artificial sequence
<220> FEATURE:
<223> OTHER INFORMATION: synthetic nucleic acid

<400> SEQUENCE: 3
gtctcgtggg ctcggagatg tgtataagag acagcagtgg gaagactgat ggagcctta      59

<210> SEQ ID NO 4
<211> LENGTH: 53
<212> TYPE: DNA
<213> ORGANISM: Artificial sequence
<220> FEATURE:
<223> OTHER INFORMATION: Synthetic oligonucleotide

<400> SEQUENCE: 4
tcgtcggcag cgtcagatgt gtataagaga cagatggaca cgagggcccc cac            53

<210> SEQ ID NO 5
<211> LENGTH: 58
<212> TYPE: DNA
<213> ORGANISM: Artificial sequence
<220> FEATURE:
<223> OTHER INFORMATION: Synthetic oligonucleotide

<400> SEQUENCE: 5
gtctcgtggg ctcggagatg tgtataagag acagtggtgg gaagakgagg acagtagg       58
```

```
<210> SEQ ID NO 6
<211> LENGTH: 58
<212> TYPE: DNA
<213> ORGANISM: Artificial sequence
<220> FEATURE:
<223> OTHER INFORMATION: Synthetic oligonucleotide

<400> SEQUENCE: 6
gtctcgtggg ctcggagatg tgtataagag acagtggtgg gaagakgagg acactagg      58

<210> SEQ ID NO 7
<211> LENGTH: 58
<212> TYPE: DNA
<213> ORGANISM: Artificial sequence
<220> FEATURE:
<223> OTHER INFORMATION: Synthetic oligonucleotide

<400> SEQUENCE: 7
gtctcgtggg ctcggagatg tgtataagag acagtggtgg gaagakgagg acagaagg      58
```